(12) United States Patent
Morton

(10) Patent No.: US 9,791,590 B2
(45) Date of Patent: Oct. 17, 2017

(54) PORTABLE SECURITY INSPECTION SYSTEM

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 223 days.

(21) Appl. No.: 14/169,998

(22) Filed: Jan. 31, 2014

(65) Prior Publication Data

US 2014/0211916 A1    Jul. 31, 2014

Related U.S. Application Data

(60) Provisional application No. 61/759,211, filed on Jan. 31, 2013.

(51) Int. Cl.
*G01V 5/00* (2006.01)

(52) U.S. Cl.
CPC .................................. *G01V 5/0016* (2013.01)

(58) Field of Classification Search
CPC ................... G01V 5/0016–5/0066; B60S 9/12
USPC .......................................................... 378/57
See application file for complete search history.

(56) References Cited

U.S. PATENT DOCUMENTS

| | | | |
|---|---|---|---|
| 2,420,845 A | 5/1947 | Slack | |
| 2,636,619 A | 4/1953 | Alexander | |
| 2,831,123 A | 4/1958 | Daly | |
| 2,885,069 A | 5/1959 | Bowen | |
| 2,952,790 A | 9/1960 | Steen | |
| 2,971,433 A | 2/1961 | Akin | |
| 3,070,399 A | 12/1962 | Bartlett | |
| 3,073,960 A | 1/1963 | Guentner | |
| 3,146,349 A | 8/1964 | Jordan | |
| 3,239,706 A | 3/1966 | Farrell | |
| 3,275,831 A | 9/1966 | Martin | |
| 3,374,355 A | 3/1968 | Parratt | |
| 3,458,026 A | 7/1969 | Lauzon | |
| 3,485,339 A | 12/1969 | Miller | |
| 3,676,783 A | 7/1972 | Kinbara | |

(Continued)

FOREIGN PATENT DOCUMENTS

| | | |
|---|---|---|
| CN | 1947001 | 4/2007 |
| DE | 2729353 A1 | 1/1979 |

(Continued)

OTHER PUBLICATIONS

US 5,987,079, 11/1999, Scott (withdrawn)

(Continued)

*Primary Examiner* — Wyatt Stoffa
*Assistant Examiner* — Eliza Osenbaugh-Stewar
(74) *Attorney, Agent, or Firm* — Novel IP

(57) ABSTRACT

The present specification discloses a radiographic inspection system for screening an area. The inspection system has a container that defines an enclosed volume, a radiation source positioned within the enclosed volume, a detector array, a movable structure attached to a portion of the base of the container, and a controller programmed to move the movable structure to achieve an optimum height of the radiation source's field of view based upon a plurality of data.

13 Claims, 14 Drawing Sheets

(56) References Cited

U.S. PATENT DOCUMENTS

| | | |
|---|---|---|
| 3,766,387 A | 10/1973 | Heffan |
| 3,767,850 A | 10/1973 | McMillian et al. |
| 3,768,645 A | 10/1973 | Conway |
| 3,770,955 A | 11/1973 | Tomita |
| 3,784,837 A | 1/1974 | Holmstrom |
| 3,837,502 A | 9/1974 | Hornagold |
| RE28,544 E | 9/1975 | Stein |
| 3,904,923 A | 9/1975 | Schwartz |
| 3,919,467 A | 11/1975 | Peugeot |
| 3,955,678 A | 5/1976 | Moyer |
| 3,961,186 A | 6/1976 | Leunbach |
| 3,980,889 A | 9/1976 | Haas |
| 4,047,035 A | 9/1977 | Dennhoven |
| 4,057,725 A | 11/1977 | Wagner |
| 4,064,440 A | 12/1977 | Roder |
| 4,105,922 A | 8/1978 | Lambert |
| 4,139,771 A | 2/1979 | Dennhoven |
| 4,164,138 A | 8/1979 | Burkhart |
| 4,203,036 A | 5/1980 | Tschunt |
| 4,210,811 A | 7/1980 | Dennhoven |
| 4,216,499 A | 8/1980 | Dennhoven |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura |
| 4,340,816 A | 7/1982 | Schott |
| 4,352,021 A | 9/1982 | Boyd |
| 4,366,382 A | 12/1982 | Kotowski |
| 4,380,817 A | 4/1983 | Harding |
| 4,430,568 A | 2/1984 | Yoshida |
| 4,468,802 A | 8/1984 | Friedel |
| 4,481,403 A | 11/1984 | Del Monte |
| 4,501,011 A | 2/1985 | Hauck |
| 4,525,854 A | 6/1985 | Molbert |
| 4,563,707 A | 1/1986 | Kishida |
| 4,566,113 A | 1/1986 | Doenges |
| 4,599,740 A | 7/1986 | Cable |
| 4,626,688 A | 12/1986 | Barnes |
| 4,641,330 A | 2/1987 | Herwig |
| 4,672,649 A | 6/1987 | Rutt |
| 4,675,890 A | 6/1987 | Plessis |
| 4,709,382 A | 11/1987 | Sones |
| 4,736,401 A | 4/1988 | Donges |
| 4,752,948 A | 6/1988 | MacMahon |
| 4,754,469 A | 6/1988 | Harding |
| 4,788,704 A | 11/1988 | Donges |
| 4,789,930 A | 12/1988 | Sones |
| 4,799,247 A | 1/1989 | Annis |
| 4,809,312 A | 2/1989 | Annis |
| 4,809,857 A | 3/1989 | Steuck |
| 4,817,123 A | 3/1989 | Sones |
| 4,825,454 A | 4/1989 | Annis |
| 4,831,260 A | 5/1989 | DiBianca |
| RE32,961 E | 6/1989 | Wagner |
| 4,853,595 A | 8/1989 | Alfano |
| 4,864,142 A | 9/1989 | Gomberg |
| 4,866,439 A | 9/1989 | Kraus |
| 4,866,745 A | 9/1989 | Akai |
| 4,868,856 A | 9/1989 | Frith |
| 4,870,670 A | 9/1989 | Geus |
| 4,872,188 A | 10/1989 | Lauro |
| 4,879,735 A | 11/1989 | Owens |
| 4,884,289 A | 11/1989 | Glockmann |
| 4,887,604 A | 12/1989 | Shefer |
| 4,956,856 A | 9/1990 | Harding |
| 4,975,917 A | 12/1990 | Villa |
| 4,979,137 A | 12/1990 | Gerstenfeld |
| 4,979,202 A | 12/1990 | Siczek |
| 4,987,584 A | 1/1991 | Doenges |
| 4,991,189 A | 2/1991 | Boomgaarden |
| 4,991,708 A | 2/1991 | Francioni |
| 5,006,299 A | 4/1991 | Gozani |
| 5,007,072 A | 4/1991 | Jenkins |
| 5,008,911 A | 4/1991 | Harding |
| 5,014,293 A | 5/1991 | Boyd |
| 5,022,062 A | 6/1991 | Annis |
| 5,033,106 A | 7/1991 | Kita |
| 5,040,199 A | 8/1991 | Stein |
| 5,065,418 A * | 11/1991 | Bermbach ............ G01V 5/0016 250/358.1 |
| 5,067,145 A | 11/1991 | Siczek |
| 5,076,993 A | 12/1991 | Sawa |
| 5,086,300 A | 2/1992 | Ashmore |
| 5,091,924 A | 2/1992 | Bermbach |
| 5,092,451 A | 3/1992 | Jones |
| 5,097,939 A | 3/1992 | Shanklin |
| 5,098,640 A | 3/1992 | Gozani |
| 5,114,662 A | 5/1992 | Gozani |
| 5,144,191 A | 9/1992 | Jones |
| 5,179,581 A | 1/1993 | Annis |
| 5,181,234 A | 1/1993 | Smith |
| 5,182,764 A | 1/1993 | Peschmann |
| 5,185,778 A | 2/1993 | Magram |
| 5,202,932 A | 4/1993 | Cambier |
| 5,221,843 A | 6/1993 | Alvarez |
| 5,224,144 A | 6/1993 | Annis |
| 5,237,598 A | 8/1993 | Albert |
| 5,243,693 A | 9/1993 | Maron |
| 5,247,556 A | 9/1993 | Eckert |
| 5,247,561 A | 9/1993 | Kotowski |
| 5,253,283 A | 10/1993 | Annis |
| 5,259,014 A | 11/1993 | Brettschneider |
| 5,260,983 A | 11/1993 | Ono |
| 5,263,075 A | 11/1993 | McGann |
| 5,265,144 A | 11/1993 | Harding |
| 5,272,627 A | 12/1993 | Maschhoff |
| 5,313,511 A | 5/1994 | Annis |
| 5,319,547 A | 6/1994 | Krug |
| 5,321,271 A | 6/1994 | Schonberg |
| 5,341,916 A | 8/1994 | Doane |
| 5,367,552 A | 11/1994 | Peschmann |
| 5,379,334 A | 1/1995 | Zimmer |
| 5,394,454 A | 2/1995 | Harding |
| 5,410,156 A | 4/1995 | Miller |
| 5,412,702 A | 5/1995 | Sata |
| 5,417,540 A * | 5/1995 | Cox ..................... B60P 1/6427 414/495 |
| 5,418,372 A | 5/1995 | Schonberg |
| 5,420,905 A | 5/1995 | Bertozzi |
| 5,430,787 A | 7/1995 | Norton |
| 5,467,377 A | 11/1995 | Dawson |
| 5,490,196 A | 2/1996 | Rudich |
| 5,490,218 A | 2/1996 | Krug |
| 5,493,596 A | 2/1996 | Annis |
| 5,505,291 A | 4/1996 | Huang |
| 5,511,104 A | 4/1996 | Mueller |
| 5,524,133 A | 6/1996 | Neale |
| 5,548,123 A | 8/1996 | Perez-Mendez |
| 5,548,630 A | 8/1996 | Hell |
| 5,557,108 A | 9/1996 | Tumer |
| 5,590,057 A | 12/1996 | Fletcher |
| 5,600,303 A | 2/1997 | Husseiny |
| 5,600,700 A | 2/1997 | Krug |
| 5,602,890 A * | 2/1997 | Gray ..................... B07C 5/3404 378/56 |
| 5,602,894 A | 2/1997 | Bardash |
| 5,604,778 A | 2/1997 | Polacin |
| 5,606,167 A | 2/1997 | Miller |
| 5,633,907 A | 5/1997 | Gravelle |
| 5,634,551 A | 6/1997 | Francioni |
| 5,638,420 A | 6/1997 | Armistead |
| 5,638,817 A | 6/1997 | Morgan |
| 5,642,393 A | 6/1997 | Krug |
| 5,642,394 A | 6/1997 | Rothschild |
| 5,660,549 A | 8/1997 | Witt |
| 5,661,377 A | 8/1997 | Mishin |
| 5,661,774 A | 8/1997 | Gordon |
| 5,666,393 A | 9/1997 | Annis |
| 5,687,210 A | 11/1997 | Maitrejean |
| 5,689,541 A | 11/1997 | Schardt |
| 5,692,028 A | 11/1997 | Geus |
| 5,692,029 A | 11/1997 | Husseiny |
| 5,696,806 A | 12/1997 | Grodzins |
| 5,712,926 A | 1/1998 | Eberhard |

(56) References Cited

U.S. PATENT DOCUMENTS

| | | |
|---|---|---|
| 5,738,202 A | 4/1998 | Ydoate |
| 5,744,919 A | 4/1998 | Mishin |
| 5,745,543 A | 4/1998 | De Bokx |
| 5,751,837 A | 5/1998 | Watanabe |
| 5,763,886 A | 6/1998 | Schulte |
| 5,763,903 A | 6/1998 | Mandai |
| 5,764,683 A | 6/1998 | Swift |
| 5,768,334 A | 6/1998 | Maitrejean |
| 5,787,145 A | 7/1998 | Geus |
| 5,796,802 A | 8/1998 | Gordon |
| 5,805,660 A | 9/1998 | Perion |
| 5,818,897 A | 10/1998 | Gordon |
| 5,838,758 A | 11/1998 | Krug |
| 5,838,759 A | 11/1998 | Armistead |
| 5,841,831 A | 11/1998 | Hell |
| 5,842,578 A | 12/1998 | Cordeiro |
| 5,859,891 A | 1/1999 | Hibbard |
| 5,870,449 A | 2/1999 | Lee |
| 5,881,122 A | 3/1999 | Crawford |
| 5,882,206 A | 3/1999 | Gillio |
| 5,887,047 A | 3/1999 | Bailey |
| 5,901,198 A | 5/1999 | Crawford |
| 5,903,623 A | 5/1999 | Swift |
| 5,905,806 A | 5/1999 | Eberhard |
| 5,909,477 A | 6/1999 | Crawford |
| 5,909,478 A | 6/1999 | Polichar |
| 5,910,973 A | 6/1999 | Grodzins |
| 5,930,326 A | 7/1999 | Rothschild |
| 5,940,468 A | 8/1999 | Huang |
| 5,949,811 A | 9/1999 | Baba |
| 5,949,842 A | 9/1999 | Schafer |
| 5,963,211 A | 10/1999 | Oikawa |
| 5,966,422 A | 10/1999 | Dafni |
| 5,970,113 A | 10/1999 | Crawford |
| 5,974,111 A | 10/1999 | Krug |
| 5,982,843 A | 11/1999 | Bailey |
| 5,987,097 A | 11/1999 | Salasoo |
| 6,018,562 A | 1/2000 | Willson |
| 6,021,174 A | 2/2000 | Campbell |
| 6,026,143 A | 2/2000 | Simanovsky |
| 6,026,171 A | 2/2000 | Hiraoglu |
| 6,031,888 A | 2/2000 | Ivan |
| 6,031,890 A | 2/2000 | Bermbach |
| 6,032,808 A | 3/2000 | Henson |
| 6,035,014 A | 3/2000 | Hiraoglu |
| 6,037,597 A | 3/2000 | Karavolos |
| 6,044,353 A | 3/2000 | Pugliese |
| 6,054,712 A | 4/2000 | Komardin |
| 6,056,671 A | 5/2000 | Marmer |
| 6,058,158 A | 5/2000 | Eiler |
| 6,067,344 A | 5/2000 | Grodzins |
| 6,067,366 A | 5/2000 | Simanovsky |
| 6,073,751 A | 6/2000 | Worzischek |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,850 A | 9/2000 | Mayo |
| 6,118,852 A | 9/2000 | Rogers |
| 6,122,343 A | 9/2000 | Pidcock |
| 6,125,165 A | 9/2000 | Warburton |
| 6,128,365 A | 10/2000 | Bechwati |
| 6,134,299 A | 10/2000 | Artig |
| 6,137,895 A | 10/2000 | Al-Sheikh |
| 6,149,592 A | 11/2000 | Yanof |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,185,272 B1 | 2/2001 | Hiraoglu |
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,200,024 B1 | 3/2001 | Negrelli |
| 6,212,251 B1 | 4/2001 | Tomura |
| 6,216,540 B1 | 4/2001 | Nelson |
| 6,218,943 B1 | 4/2001 | Ellenbogen |
| 6,236,709 B1 | 5/2001 | Perry |
| 6,236,712 B1 | 5/2001 | Tomasetti |
| 6,246,320 B1 | 6/2001 | Monroe |
| 6,249,567 B1 | 6/2001 | Rothschild |
| 6,252,929 B1 | 6/2001 | Swift |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis |
| 6,282,260 B1 | 8/2001 | Grodzins |
| 6,292,533 B1 | 9/2001 | Swift |
| 6,301,326 B2 | 10/2001 | Bjorkholm |
| 6,301,327 B1 | 10/2001 | Martens |
| 6,304,629 B1 | 10/2001 | Conway |
| 6,317,509 B1 | 11/2001 | Simanovsky |
| 6,320,933 B1 | 11/2001 | Grodzins |
| 6,324,249 B1 | 11/2001 | Fazzio |
| 6,345,113 B1 | 2/2002 | Crawford |
| 6,347,132 B1 | 2/2002 | Annis |
| 6,356,620 B1 | 3/2002 | Rothschild |
| 6,396,899 B2 | 5/2002 | Kuwabara |
| 6,418,189 B1 | 7/2002 | Schafer |
| 6,418,194 B1 | 7/2002 | McPherson |
| 6,421,420 B1 | 7/2002 | Grodzins |
| 6,424,695 B1 | 7/2002 | Grodzins |
| 6,427,891 B1 | 8/2002 | Anderson |
| 6,429,578 B1 | 8/2002 | Danielsson |
| 6,430,255 B2 | 8/2002 | Fenkart |
| 6,431,344 B1 | 8/2002 | Emmermann |
| 6,434,219 B1 | 8/2002 | Rothschild |
| 6,435,715 B1 | 8/2002 | Betz |
| 6,438,201 B1 | 8/2002 | Mazess |
| 6,442,233 B1 | 8/2002 | Grodzins |
| 6,445,765 B1 | 9/2002 | Frank |
| 6,446,782 B1 | 9/2002 | Patrick |
| 6,448,564 B1 | 9/2002 | Johnson |
| 6,453,003 B1 | 9/2002 | Springer |
| 6,453,007 B2 | 9/2002 | Adams |
| 6,456,684 B1 | 9/2002 | Mun |
| 6,459,755 B1 | 10/2002 | Li |
| 6,459,761 B1 | 10/2002 | Grodzins |
| 6,459,764 B1 | 10/2002 | Chalmers |
| 6,473,487 B1 | 10/2002 | Le |
| RE37,899 E | 11/2002 | Grodzins |
| 6,483,894 B2 | 11/2002 | Hartick |
| 6,507,025 B1 | 1/2003 | Verbinski |
| 6,528,787 B2 | 3/2003 | Katagami |
| 6,532,276 B1 | 3/2003 | Hartick |
| 6,542,574 B2 | 4/2003 | Grodzins |
| 6,542,578 B2 | 4/2003 | Ries |
| 6,542,580 B1 * | 4/2003 | Carver ............ G01V 5/0008 378/57 |
| 6,542,754 B1 | 4/2003 | Sayers |
| 6,543,599 B2 | 4/2003 | Jasinetzky |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,563,906 B2 | 5/2003 | Hussein |
| 6,567,496 B1 | 5/2003 | Sychev |
| 6,580,778 B2 | 6/2003 | Meder |
| 6,584,170 B2 | 6/2003 | Aust |
| 6,590,956 B2 | 7/2003 | Fenkart |
| 6,591,130 B2 | 7/2003 | Shahidi |
| 6,597,760 B2 | 7/2003 | Beneke |
| 6,605,473 B1 | 8/2003 | Hajduk |
| 6,606,516 B2 | 8/2003 | Levine |

(56) References Cited

U.S. PATENT DOCUMENTS

| | | |
|---|---|---|
| 6,618,466 B1 | 9/2003 | Ning |
| 6,621,888 B2 | 9/2003 | Grodzins |
| 6,628,745 B1 | 9/2003 | Annis |
| 6,629,593 B2 | 10/2003 | Zeitler |
| 6,636,581 B2 | 10/2003 | Sorenson |
| 6,636,623 B2 | 10/2003 | Nelson |
| 6,647,091 B2 | 11/2003 | Fenkart |
| 6,647,094 B2 | 11/2003 | Harding |
| 6,647,095 B2 | 11/2003 | Hsieh |
| 6,653,588 B1 | 11/2003 | Gillard-Hickman |
| 6,658,087 B2 | 12/2003 | Chalmers |
| 6,661,876 B2 | 12/2003 | Turner |
| 6,663,280 B2 | 12/2003 | Doenges |
| 6,665,373 B1 | 12/2003 | Kotowski |
| 6,665,433 B2 | 12/2003 | Roder |
| 6,687,333 B2 | 2/2004 | Carroll |
| 6,690,766 B2 | 2/2004 | Kresse |
| 6,702,459 B2 | 3/2004 | Barnes |
| 6,707,879 B2 | 3/2004 | McClelland |
| 6,713,773 B1 | 3/2004 | Lyons |
| 6,715,533 B2 | 4/2004 | Kresse |
| 6,721,387 B1 | 4/2004 | Naidu |
| 6,721,391 B2 | 4/2004 | McClelland |
| 6,727,506 B2 | 4/2004 | Mallette |
| 6,735,271 B1 | 5/2004 | Rand |
| 6,735,279 B1 | 5/2004 | Jacobs |
| 6,737,652 B2 | 5/2004 | Lanza |
| 6,744,845 B2 | 6/2004 | Harding |
| 6,748,043 B1 | 6/2004 | Dobbs |
| 6,754,298 B2 | 6/2004 | Fessler |
| 6,760,407 B2 | 7/2004 | Price |
| 6,763,083 B2 | 7/2004 | Fernandez |
| 6,763,635 B1 | 7/2004 | Lowman |
| 6,770,884 B2 | 8/2004 | Bryman |
| 6,775,348 B2 | 8/2004 | Hoffman |
| 6,785,357 B2 | 8/2004 | Bernardi |
| 6,788,761 B2 | 9/2004 | Bijjani |
| 6,798,863 B2 | 9/2004 | Sato |
| 6,812,426 B1 | 11/2004 | Kotowski |
| 6,813,374 B1 | 11/2004 | Karimi |
| 6,816,571 B2 | 11/2004 | Bijjani |
| 6,827,265 B2 | 12/2004 | Knowles |
| 6,829,585 B1 | 12/2004 | Grewal |
| 6,830,185 B2 | 12/2004 | Tsikos |
| 6,837,422 B1 | 1/2005 | Meder |
| 6,837,432 B2 | 1/2005 | Tsikos |
| 6,839,134 B2 | 1/2005 | Saito |
| 6,839,403 B1 | 1/2005 | Kotowski |
| 6,843,599 B2 | 1/2005 | Le |
| 6,856,344 B2 | 2/2005 | Franz |
| 6,856,667 B2 | 2/2005 | Ellenbogen |
| 6,859,514 B2 | 2/2005 | Hoffman |
| 6,869,217 B2 | 3/2005 | Rasche |
| 6,876,719 B2 | 4/2005 | Ozaki |
| 6,876,724 B2 | 4/2005 | Zhou |
| 6,879,657 B2 | 4/2005 | Hoffman |
| 6,899,540 B1 | 5/2005 | Neiderman |
| 6,901,135 B2 | 5/2005 | Fox |
| 6,901,346 B2 | 5/2005 | Tracy |
| 6,906,329 B2 | 6/2005 | Bryman |
| 6,907,101 B2 | 6/2005 | Hoffman |
| 6,920,197 B2 | 7/2005 | Kang |
| 6,922,455 B2 | 7/2005 | Jurczyk |
| 6,922,460 B2 | 7/2005 | Skatter |
| 6,922,461 B2 | 7/2005 | Kang |
| 6,928,141 B2 | 8/2005 | Carver |
| 6,933,504 B2 | 8/2005 | Hoffman |
| 6,934,354 B2 | 8/2005 | Hoffman |
| 6,937,692 B2 | 8/2005 | Johnson |
| 6,940,071 B2 | 9/2005 | Ramsden |
| 6,944,264 B2 | 9/2005 | Bijjani |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey |
| 6,953,935 B1 | 10/2005 | Hoffman |
| 6,957,913 B2 | 10/2005 | Renkart |
| 6,962,289 B2 | 11/2005 | Vatan |
| 6,965,314 B2 | 11/2005 | Bohinc, Jr. |
| 6,968,030 B2 | 11/2005 | Hoffman |
| 6,968,034 B2 | 11/2005 | Ellenbogen |
| 6,971,577 B2 | 12/2005 | Tsikos |
| 6,973,158 B2 | 12/2005 | Besson |
| 6,975,698 B2 | 12/2005 | Katcha |
| 6,978,936 B2 | 12/2005 | Tsikos |
| 6,980,627 B2 | 12/2005 | Qiu |
| 6,990,171 B2 | 1/2006 | Toth |
| 6,990,172 B2 | 1/2006 | Toth |
| 6,991,371 B2 | 1/2006 | Georgeson |
| 6,993,115 B2 | 1/2006 | McGuire |
| 6,996,209 B2 | 2/2006 | Marek |
| 7,010,083 B2 | 3/2006 | Hoffman |
| 7,010,094 B2 | 3/2006 | Grodzins |
| 7,016,459 B2 | 3/2006 | Ellenbogen |
| 7,020,241 B2 | 3/2006 | Beneke |
| 7,020,242 B2 | 3/2006 | Ellenbogen |
| 7,023,956 B2 | 4/2006 | Heaton |
| 7,023,957 B2 | 4/2006 | Bijjani |
| 7,027,553 B2 | 4/2006 | Dunham |
| 7,027,554 B2 | 4/2006 | Gaultier |
| 7,031,430 B2 | 4/2006 | Kaucic |
| 7,031,434 B1 | 4/2006 | Saunders |
| 7,034,313 B2 | 4/2006 | Hoffman |
| 7,039,154 B1 | 5/2006 | Ellenbogen |
| 7,039,159 B2 | 5/2006 | Muenchau |
| 7,042,975 B2 | 5/2006 | Heuscher |
| 7,045,787 B1 | 5/2006 | Verbinski |
| 7,045,788 B2 | 5/2006 | Iwatschenko-Borho |
| 7,046,756 B2 | 5/2006 | Hoffman |
| 7,046,761 B2 | 5/2006 | Ellenbogen |
| 7,046,768 B1 | 5/2006 | Gilevich |
| 7,050,536 B1 | 5/2006 | Fenkart |
| 7,050,541 B2 | 5/2006 | Bittl |
| 7,054,408 B2 | 5/2006 | Jiang |
| 7,062,009 B2 | 6/2006 | Karimi |
| 7,062,011 B1 | 6/2006 | Tybinkowski |
| 7,062,074 B1 | 6/2006 | Beneke |
| 7,064,334 B2 | 6/2006 | Hoffman |
| 7,065,175 B2 | 6/2006 | Green |
| 7,065,179 B2 | 6/2006 | Block |
| 7,068,749 B2 | 6/2006 | Kollegal |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,081,628 B2 | 7/2006 | Granfors |
| 7,084,404 B2 | 8/2006 | Hoffman |
| 7,087,902 B2 | 8/2006 | Wang |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,099,434 B2 | 8/2006 | Adams |
| 7,099,435 B2 | 8/2006 | Heumann |
| 7,103,137 B2 | 9/2006 | Seppi |
| 7,110,488 B2 | 9/2006 | Katcha |
| 7,112,797 B2 | 9/2006 | Hoge |
| 7,116,235 B2 | 10/2006 | Alioto |
| 7,116,749 B2 | 10/2006 | Besson |
| 7,116,751 B2 | 10/2006 | Ellenbogen |
| 7,119,553 B2 | 10/2006 | Yang |
| 7,123,681 B2 | 10/2006 | Ellenbogen |
| 7,127,027 B2 | 10/2006 | Hoffman |
| 7,130,374 B1 | 10/2006 | Jacobs |
| RE39,396 E | 11/2006 | Swift |
| 7,133,491 B2 | 11/2006 | Bernardi |
| 7,136,450 B2 | 11/2006 | Ying |
| 7,136,451 B2 | 11/2006 | Naidu |
| 7,139,367 B1 | 11/2006 | Le |
| 7,139,406 B2 | 11/2006 | McClelland |
| 7,142,208 B2 | 11/2006 | Lorenz |
| 7,142,629 B2 | 11/2006 | Edic |
| 7,149,278 B2 | 12/2006 | Arenson |

(56) References Cited

U.S. PATENT DOCUMENTS

| | | |
|---|---|---|
| 7,149,339 B2 | 12/2006 | Veneruso |
| 7,151,447 B1 | 12/2006 | Willms |
| 7,154,989 B2 | 12/2006 | Ueno |
| 7,155,812 B1 | 1/2007 | Peterson |
| 7,158,611 B2 | 1/2007 | Heismann |
| 7,162,005 B2 | 1/2007 | Bjorkholm |
| 7,162,285 B2 | 1/2007 | Owens |
| 7,164,747 B2 | 1/2007 | Ellenbogen |
| 7,164,750 B2 | 1/2007 | Nabors |
| 7,166,458 B2 | 1/2007 | Ballerstadt |
| 7,166,844 B1 | 1/2007 | Gormley |
| 7,167,539 B1 | 1/2007 | Hoffman |
| 7,173,998 B2 | 2/2007 | Hoffman |
| 7,177,387 B2 | 2/2007 | Yasunaga |
| 7,177,391 B2 | 2/2007 | Chapin |
| 7,187,756 B2 | 3/2007 | Gohno |
| 7,190,757 B2 | 3/2007 | Ying |
| 7,192,031 B2 | 3/2007 | Dunham |
| 7,197,113 B1 | 3/2007 | Katcha |
| 7,197,172 B1 | 3/2007 | Naidu |
| 7,203,276 B2 | 4/2007 | Arsenault |
| 7,203,629 B2 | 4/2007 | Oezis |
| 7,204,125 B2 | 4/2007 | Fine |
| 7,206,379 B2 | 4/2007 | Lemaitre |
| 7,207,713 B2 | 4/2007 | Lowman |
| 7,212,113 B2 | 5/2007 | Zanovitch |
| 7,215,731 B1 | 5/2007 | Basu |
| 7,215,737 B2 | 5/2007 | Li |
| 7,215,738 B2 | 5/2007 | Muenchau |
| 7,218,700 B2 | 5/2007 | Huber |
| 7,218,704 B1 | 5/2007 | Adams |
| 7,224,763 B2 | 5/2007 | Naidu |
| 7,224,765 B2 | 5/2007 | Ellenbogen |
| 7,224,766 B2 | 5/2007 | Jiang |
| 7,224,769 B2 | 5/2007 | Turner |
| 7,233,640 B2 | 6/2007 | Ikhlef |
| 7,236,564 B2 | 6/2007 | Hopkins |
| 7,238,945 B2 | 7/2007 | Hoffman |
| 7,238,951 B2 | 7/2007 | Disdier |
| 7,244,947 B2 | 7/2007 | Polichar |
| 7,247,856 B2 | 7/2007 | Hoge |
| 7,250,940 B2 | 7/2007 | Jayanetti |
| 7,251,310 B2 | 7/2007 | Smith |
| 7,257,189 B2 | 8/2007 | Modica |
| 7,260,170 B2 | 8/2007 | Arenson |
| 7,260,171 B1 | 8/2007 | Arenson |
| 7,260,172 B2 | 8/2007 | Arenson |
| 7,260,173 B2 | 8/2007 | Wakayama |
| 7,260,174 B2 | 8/2007 | Hoffman |
| 7,260,182 B2 | 8/2007 | Toth |
| 7,260,255 B2 | 8/2007 | Polichar |
| 7,263,160 B2 | 8/2007 | Schlomka |
| 7,266,180 B1 | 9/2007 | Saunders |
| 7,272,208 B2 | 9/2007 | Yatsenko |
| 7,272,429 B2 | 9/2007 | Walker |
| 7,274,767 B2 | 9/2007 | Clayton |
| 7,277,526 B2 | 10/2007 | Rifkin |
| 7,277,577 B2 | 10/2007 | Ying |
| 7,279,120 B2 | 10/2007 | Cheng |
| 7,280,631 B2 | 10/2007 | De Man |
| 7,282,727 B2 | 10/2007 | Retsky |
| 7,283,604 B2 | 10/2007 | De Man |
| 7,283,609 B2 | 10/2007 | Possin |
| 7,295,019 B2 | 11/2007 | Yang |
| 7,295,651 B2 | 11/2007 | Delgado |
| 7,298,812 B2 | 11/2007 | Tkaczyk |
| 7,302,083 B2 | 11/2007 | Larson |
| 7,308,073 B2 | 12/2007 | Tkaczyk |
| 7,308,074 B2 | 12/2007 | Jiang |
| 7,308,077 B2 | 12/2007 | Bijjani |
| 7,317,195 B2 | 1/2008 | Eikman |
| 7,317,259 B2 | 1/2008 | Yamauchi |
| 7,317,390 B2 | 1/2008 | Huey |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying |
| 7,330,527 B2 | 2/2008 | Hoffman |
| 7,330,535 B2 | 2/2008 | Arenson |
| 7,333,587 B2 | 2/2008 | De Man |
| 7,333,588 B2 | 2/2008 | Mistretta |
| 7,333,589 B2 | 2/2008 | Ellenbogen |
| 7,335,887 B1 | 2/2008 | Verbinski |
| 7,336,769 B2 | 2/2008 | Arenson |
| 7,349,525 B2 | 3/2008 | Morton |
| 7,352,843 B2 | 4/2008 | Hu |
| 7,356,174 B2 | 4/2008 | Leue |
| 7,369,463 B1 | 5/2008 | Van Dullemen |
| 7,369,640 B2 | 5/2008 | Seppi |
| 7,369,643 B2 | 5/2008 | Kotowski |
| 7,372,040 B2 | 5/2008 | Polichar |
| 7,372,944 B2 | 5/2008 | Bernhardt |
| 7,379,530 B2 | 5/2008 | Hoff |
| 7,386,092 B2 | 6/2008 | Kang |
| 7,397,891 B2 | 7/2008 | Johnson |
| 7,400,701 B1 | 7/2008 | Cason |
| 7,420,174 B2 | 9/2008 | Kurita |
| 7,429,738 B2 | 9/2008 | Li |
| 7,440,543 B2 | 10/2008 | Morton |
| 7,453,987 B1 | 11/2008 | Richardson |
| 7,460,639 B2 | 12/2008 | Tudor |
| 7,470,914 B2 | 12/2008 | Li |
| 7,475,428 B2 | 1/2009 | Smith |
| 7,475,866 B2 | 1/2009 | Hu |
| 7,483,510 B2 | 1/2009 | Carver |
| 7,483,511 B2 | 1/2009 | Bendahan |
| 7,486,768 B2 | 2/2009 | Allman |
| 7,492,855 B2 | 2/2009 | Hopkins |
| 7,500,931 B2 | 3/2009 | Rosemeier |
| 7,505,556 B2 | 3/2009 | Chalmers |
| 7,505,557 B2 | 3/2009 | Modica |
| 7,505,562 B2 | 3/2009 | Dinca |
| 7,512,215 B2 | 3/2009 | Morton |
| 7,517,149 B2 | 4/2009 | Agrawal |
| 7,519,148 B2 | 4/2009 | Kotowski |
| 7,525,101 B2 | 4/2009 | Grodzins |
| 7,526,064 B2 | 4/2009 | Akery |
| 7,538,325 B2 | 5/2009 | Mishin |
| 7,547,888 B2 | 6/2009 | Cooke |
| 7,551,714 B2 | 6/2009 | Rothschild |
| 7,551,715 B2 | 6/2009 | Rothschild |
| 7,551,718 B2 | 6/2009 | Rothschild |
| 7,555,099 B2 | 6/2009 | Rothschild |
| 7,564,939 B2 | 7/2009 | Morton |
| 7,580,505 B2 | 8/2009 | Kang |
| 7,593,506 B2 | 9/2009 | Cason |
| 7,593,510 B2 | 9/2009 | Rothschild |
| 7,609,807 B2 | 10/2009 | Leue |
| 7,649,976 B2 | 1/2010 | Georgeson |
| 7,663,109 B2 | 2/2010 | Kang |
| 7,684,538 B2 | 3/2010 | Morton |
| 7,720,195 B2 | 5/2010 | Allman |
| 7,724,869 B2 | 5/2010 | Wang |
| 7,734,066 B2 | 6/2010 | DeLia |
| 7,738,687 B2 | 6/2010 | Tortora |
| 7,741,612 B2 | 6/2010 | Clothier |
| 7,742,568 B2 | 6/2010 | Smith |
| 7,760,103 B2 | 7/2010 | Frank |
| 7,762,760 B2 | 7/2010 | Takehara |
| 7,769,133 B2 | 8/2010 | Carver |
| 7,783,003 B2 | 8/2010 | Clayton |
| 7,783,004 B2 | 8/2010 | Kotowski |
| 7,796,734 B2 | 9/2010 | Mastronardi |
| 7,800,073 B2 | 9/2010 | Clothier |
| 7,809,104 B2 | 10/2010 | Foland |
| 7,809,109 B2 | 10/2010 | Mastronardi |
| 7,817,775 B2 | 10/2010 | Kang |
| 7,817,776 B2 | 10/2010 | Agrawal |
| 7,835,486 B2 | 11/2010 | Basu |
| 7,844,028 B2 | 11/2010 | Korsunsky |
| 7,860,213 B2 | 12/2010 | Akery |
| 7,876,879 B2 | 1/2011 | Morton |
| 7,876,880 B2 | 1/2011 | Kotowski |
| 7,885,375 B2 | 2/2011 | Bernard |

(56) References Cited

U.S. PATENT DOCUMENTS

| | | |
|---|---|---|
| 7,903,783 B2 | 3/2011 | Modica |
| 7,952,079 B2 | 5/2011 | Neustadter |
| 7,957,506 B2 | 6/2011 | Smith |
| 7,963,695 B2 | 6/2011 | Kotowski |
| 7,965,695 B2 | 6/2011 | Valko |
| 7,973,697 B2 | 7/2011 | Reilly |
| 7,991,113 B2 | 8/2011 | Carver |
| 7,991,117 B2 | 8/2011 | Chen |
| 7,995,705 B2 | 8/2011 | Allman |
| 8,000,436 B2 | 8/2011 | Seppi |
| 8,031,903 B2 | 10/2011 | Paresi |
| 8,059,781 B2 | 11/2011 | Agrawal |
| 8,073,099 B2 | 12/2011 | Niu |
| 8,148,693 B2 | 4/2012 | Ryge |
| 8,170,177 B2 | 5/2012 | Akery |
| 8,173,970 B2 | 5/2012 | Inbar |
| 8,194,822 B2 | 6/2012 | Rothschild |
| 8,263,938 B2 | 9/2012 | Bjorkholm |
| 8,275,091 B2 | 9/2012 | Morton |
| 8,350,747 B2 | 1/2013 | Delia |
| 8,356,937 B2 | 1/2013 | Kotowski |
| 8,385,501 B2 | 2/2013 | Allman |
| 8,389,941 B2 | 3/2013 | Bendahan |
| 8,389,942 B2 | 3/2013 | Morton |
| 8,401,147 B2 | 3/2013 | Ryge |
| 8,433,036 B2 | 4/2013 | Morton |
| 8,437,448 B2 | 5/2013 | Langeveld |
| 8,451,974 B2 | 5/2013 | Morton |
| 8,457,275 B2 | 6/2013 | Akery |
| 8,483,356 B2 | 7/2013 | Bendahan |
| 8,491,189 B2 | 7/2013 | Kotowski |
| 8,498,376 B2 | 7/2013 | Modica |
| 8,502,699 B2 | 8/2013 | Zerwekh |
| 8,503,605 B2 | 8/2013 | Morton |
| 8,579,506 B2 | 11/2013 | Morton |
| 8,582,720 B2 | 11/2013 | Morton |
| 8,644,453 B2 | 2/2014 | Morton |
| 8,668,386 B2 | 3/2014 | Morton |
| 8,687,765 B2 | 4/2014 | Kotowski |
| 8,735,833 B2 | 5/2014 | Morton |
| 8,744,033 B2 | 6/2014 | Oosaka |
| 8,798,232 B2 | 8/2014 | Bendahan |
| 8,831,176 B2 | 9/2014 | Morton |
| 8,837,670 B2 | 9/2014 | Akery |
| 8,929,509 B2 | 1/2015 | Morton |
| 9,057,679 B2 | 6/2015 | Morton |
| 2002/0031202 A1 | 3/2002 | Callerame |
| 2002/0038753 A1 | 4/2002 | Ursu |
| 2002/0045152 A1 | 4/2002 | Viscardi |
| 2003/0023592 A1 | 1/2003 | Modica |
| 2003/0085163 A1 | 5/2003 | Chan |
| 2004/0017888 A1 | 1/2004 | Seppi |
| 2004/0086078 A1 | 5/2004 | Adams |
| 2004/0101098 A1 | 5/2004 | Bijjani |
| 2004/0125914 A1 | 7/2004 | Kang |
| 2004/0141584 A1 | 7/2004 | Bernardi |
| 2004/0178339 A1 | 9/2004 | Gentile |
| 2004/0213378 A1 | 10/2004 | Zhou |
| 2004/0258198 A1 | 12/2004 | Carver |
| 2004/0258305 A1 | 12/2004 | Burnham |
| 2005/0008119 A1 | 1/2005 | McClelland |
| 2005/0023479 A1 | 2/2005 | Grodzins |
| 2005/0031076 A1 | 2/2005 | McClelland |
| 2005/0100135 A1 | 5/2005 | Lowman |
| 2005/0117683 A1 | 6/2005 | Mishin |
| 2005/0117700 A1 | 6/2005 | Peschmann |
| 2005/0135668 A1 | 6/2005 | Polichar |
| 2005/0156734 A1 | 7/2005 | Zerwekh |
| 2005/0157842 A1 | 7/2005 | Agrawal |
| 2005/0169421 A1 | 8/2005 | Muenchau |
| 2005/0180542 A1 | 8/2005 | Leue |
| 2005/0226364 A1 | 10/2005 | Bernard |
| 2005/0226383 A1 | 10/2005 | Rifkin |
| 2005/0251397 A1 | 11/2005 | Zanovitch |
| 2006/0056584 A1 | 3/2006 | Allman |
| 2006/0115109 A1 | 6/2006 | Whitson |
| 2006/0140341 A1 | 6/2006 | Carver |
| 2006/0176998 A1 | 8/2006 | Korsunsky |
| 2006/0274916 A1 | 12/2006 | Chan |
| 2006/0284094 A1 | 12/2006 | Inbar |
| 2007/0007455 A1 | 1/2007 | Juni |
| 2007/0009088 A1 | 1/2007 | Edic |
| 2007/0085010 A1 | 4/2007 | Letant |
| 2007/0110215 A1 | 5/2007 | Hu |
| 2007/0140423 A1 | 6/2007 | Foland |
| 2007/0172129 A1 | 7/2007 | Tortora |
| 2007/0189454 A1 | 8/2007 | Georgeson |
| 2007/0194909 A1 | 8/2007 | Garfield |
| 2007/0210255 A1 | 9/2007 | Bjorkholm |
| 2007/0269005 A1* | 11/2007 | Chalmers ............... G01N 23/20 378/57 |
| 2007/0280416 A1 | 12/2007 | Bendahan |
| 2007/0280502 A1 | 12/2007 | Paresi |
| 2007/0286337 A1 | 12/2007 | Wang |
| 2008/0037707 A1 | 2/2008 | Rothschild |
| 2008/0044801 A1 | 2/2008 | Modica |
| 2008/0056432 A1 | 3/2008 | Pack |
| 2008/0159591 A1 | 7/2008 | Ruedin |
| 2008/0211431 A1 | 9/2008 | Mishin |
| 2008/0304622 A1 | 12/2008 | Morton |
| 2009/0067575 A1 | 3/2009 | Seppi |
| 2009/0086907 A1 | 4/2009 | Smith |
| 2009/0116617 A1 | 5/2009 | Mastronardi |
| 2009/0175412 A1 | 7/2009 | Grodzins |
| 2009/0238336 A1 | 9/2009 | Akery |
| 2009/0257555 A1 | 10/2009 | Chalmers |
| 2010/0177868 A1 | 7/2010 | Smith |
| 2011/0019797 A1 | 1/2011 | Morton |
| 2011/0019799 A1 | 1/2011 | Shedlock |
| 2011/0064192 A1 | 3/2011 | Morton |
| 2011/0116597 A1 | 5/2011 | Agrawal |
| 2011/0135060 A1 | 6/2011 | Morton |
| 2011/0176660 A1 | 7/2011 | Morton |
| 2011/0216881 A1 | 9/2011 | Modica |
| 2012/0037862 A1* | 2/2012 | McCarthy ............... B60S 9/08 254/1 |
| 2012/0099710 A1 | 4/2012 | Kotowski |
| 2012/0134473 A1 | 5/2012 | Morton |
| 2012/0177176 A1 | 7/2012 | Carver |
| 2013/0001048 A1 | 1/2013 | Panesar |
| 2013/0039472 A1 | 2/2013 | Morton |

FOREIGN PATENT DOCUMENTS

| | | |
|---|---|---|
| DE | 3214910 A1 | 5/1983 |
| EP | 77018 | 4/1983 |
| EP | 0077018 A1 | 4/1983 |
| EP | 0176314 | 4/1986 |
| EP | 0261984 A2 | 3/1988 |
| EP | 0287707 | 10/1988 |
| EP | 0412190 | 2/1991 |
| EP | 0417965 | 3/1991 |
| EP | 0432568 | 6/1991 |
| EP | 0531993 A1 | 3/1993 |
| EP | 0584871 A1 | 3/1994 |
| EP | 0864884 A2 | 9/1998 |
| EP | 0919186 A2 | 6/1999 |
| EP | 0924742 A2 | 6/1999 |
| EP | 0930046 A2 | 7/1999 |
| EP | 0963925 A2 | 12/1999 |
| EP | 1277439 A1 | 1/2003 |
| EP | 1374776 A1 | 1/2004 |
| EP | 1413898 A1 | 4/2004 |
| EP | 1135700 | 3/2005 |
| EP | 1526392 | 4/2005 |
| EP | 1254384 | 1/2008 |
| EP | 2054741 | 5/2009 |
| EP | 1733213 | 2/2010 |
| EP | 2255224 | 12/2010 |
| EP | 2049888 | 5/2014 |
| FR | 2328280 A1 | 5/1977 |
| GB | 1497396 A | 1/1978 |
| GB | 1526041 A | 9/1978 |
| GB | 2015245 A | 9/1979 |

(56) References Cited

FOREIGN PATENT DOCUMENTS

| | | |
|---|---|---|
| GB | 2089109 A | 6/1982 |
| GB | 2212903 A | 8/1989 |
| GB | 2255634 A | 11/1992 |
| GB | 2277013 A | 10/1994 |
| GB | 2337032 A | 11/1999 |
| GB | 2404431 | 2/2005 |
| GB | 2409268 A | 6/2005 |
| GB | 2424065 A | 9/2006 |
| GB | 2437777 A | 11/2007 |
| GB | 2438317 A | 11/2007 |
| GB | 2470161 | 11/2010 |
| GB | 2470163 | 11/2010 |
| GB | 2470330 | 11/2010 |
| JP | 570175247 | 10/1982 |
| JP | 59016254 | 1/1984 |
| JP | 5975549 | 4/1984 |
| JP | 600015546 | 1/1985 |
| JP | 600021440 | 2/1985 |
| JP | H10211196 A | 8/1998 |
| JP | H11230918 A | 8/1999 |
| JP | 2001176408 | 6/2001 |
| JP | 2001233440 A | 8/2001 |
| JP | 2003126075 A | 5/2003 |
| JP | 2004000605 A | 1/2004 |
| JP | 2005013768 A | 1/2005 |
| WO | 9528715 A2 | 10/1995 |
| WO | 9802763 A1 | 1/1998 |
| WO | 9803889 A1 | 1/1998 |
| WO | 9820366 A1 | 5/1998 |
| WO | 9855851 A1 | 12/1998 |
| WO | 9939189 A2 | 8/1999 |
| WO | 9960387 A2 | 11/1999 |
| WO | 0033060 A2 | 6/2000 |
| WO | 0159485 | 8/2001 |
| WO | 0159485 A1 | 8/2001 |
| WO | 03051201 A2 | 6/2003 |
| WO | 03105159 | 12/2003 |
| WO | 2004010127 A1 | 1/2004 |
| WO | 2004037088 | 5/2004 |
| WO | 2004097889 | 11/2004 |
| WO | 2004111625 | 12/2004 |
| WO | 2005091227 | 9/2005 |
| WO | 2005098400 A2 | 10/2005 |
| WO | 2005121756 A2 | 12/2005 |
| WO | 2006036076 A1 | 4/2006 |
| WO | 2006045019 | 4/2006 |
| WO | 2006078691 A2 | 7/2006 |
| WO | 2006095188 | 9/2006 |
| WO | 2005084351 | 11/2006 |
| WO | 2006135586 | 12/2006 |
| WO | 2007035359 A2 | 3/2007 |
| WO | 2007051092 | 5/2007 |
| WO | 2007055720 A2 | 5/2007 |
| WO | 2007068933 A1 | 6/2007 |
| WO | 2007103216 A2 | 9/2007 |
| WO | 2008017983 A2 | 2/2008 |
| WO | 2009027667 A2 | 3/2009 |
| WO | 2009067394 | 5/2009 |
| WO | 2009088706 | 9/2009 |
| WO | 2009106803 | 9/2009 |
| WO | 2009106815 | 9/2009 |
| WO | 2009106857 | 9/2009 |
| WO | 2009141613 | 11/2009 |
| WO | 2009141615 | 11/2009 |
| WO | 2009137698 | 12/2009 |
| WO | 2009150416 A2 | 12/2009 |
| WO | 2010135620 | 1/2011 |
| WO | 2011008718 | 1/2011 |
| WO | 2011069024 A1 | 6/2011 |
| WO | 2011087861 | 7/2011 |
| WO | 2011095810 | 8/2011 |
| WO | 2012109273 | 8/2012 |
| WO | 2012174265 | 12/2012 |
| WO | 2013116549 | 8/2013 |
| WO | 2014121097 A1 | 8/2014 |

OTHER PUBLICATIONS

International Search Report for PCT/US14/14198, May 16, 2014.
International Preliminary Report on Patentability for PCT/US2014/014198, Aug. 4, 2015.
Smith C. R. et al: 'Application of 450 kV computed tomography to engine blocks with steel liners' Materials Evaluation vol. 65, No. 5, 2007, pp. 458-461, XP055108238.
International Search Report for PCT/US10/35720, date of mailing, Nov. 15, 2010, Rapiscan Security Products, Inc.
International Search Report for PCT/US2008/087654, date of mailing, Jul. 6, 2009, Rapiscan Security Products, Inc.
International preliminary report on patentability PCT/US2012/024184, issued on Aug. 13, 2013, Rapiscan Systems Inc.
International Search Report PCT/US2012/024184, mailed on Jul. 27, 2012, Rapiscan Systems Inc.
International Search Report PCT/US2012/042493, mailed on Oct. 1, 2012, Rapiscan Systems Inc.
International Search Report PCT/GB2009/000515, Feb. 23, 2010, Rapiscan Security Products, Inc.
International Search Report for PCT/GB2009/000497, Jan. 22, 2010.
International Search Report PCT/GB2009/001444, Apr. 6, 2010, Rapiscan Security Products.
International Search Report for PCT/GB2009/000556, Feb. 19, 2010, Rapiscan Security Products, Inc.
International Search Report PCT/GB2009/001277, Jul. 20, 2010, Rapiscan Systems, Inc.
Mobile X-Ray Inspection Systems, Internet Citation, Feb. 12, 2007, pp. 1-2, URL:http://web.archive.org/web/20070212000928/http://www.bombdetecti-on.com/cat--details.php?catid=20.
Molchanov P A et al: 'Nanosecond gated optical sensors for ocean optic applications' Sensors Applications Symposium, 2006, Proceedings of the 2006 IEEE Houston, Texas,USA Feb. 7-9, 2006, Piscataway, NJ, USA,IEEE, Feb. 7, 2006 (Feb. 7, 2006), pp. 147-150, XP010917671 ISBN: 978-0-7803-9580-0.
International Search Report for PCT/US10/58809; Rapiscan Systems Inc.; Apr. 19, 2011.
International Search Report for PCT/GB2009/001250, Mar. 2, 2010, Rapiscan Security Products Inc.
International Search Report for PCT/GB2009/001275, Jul. 24, 2009, Rapiscan Security Products Inc.
International Search Report for PCT/US2010/041757, mailed on Oct. 12, 2010, Rapiscan Systems Inc.
International Bureau of WIPO, International Preliminary Report on Patentability, PCT/US2005/011382, dated Oct. 19, 2006, 7 pages.
Mertz, L.N., et al, "Rotational aperture synthesis for x rays", Journal. Optical Society of America, vol. 3, Dec. 1986, pp. 2167-2170.
International Preliminary Report on Patentability, PCT/US2012/024182, issued on Aug. 13, 2013, Rapiscan Systems Inc.
International Search Report, PCT/US2012/024182 mailed on Aug. 20, 2012, Rapiscan Systems Inc.
International Search Report for PCT/US2010/061908, mailed on Apr. 2, 2012, Rapiscan Systems, Inc.
International Search Report for PCT/GB2006/000859, mailed on May 19, 2006, Corus UK Ltd.
International Search Report for PCT/GB2011/050182, Dec. 28, 2011.
International Search Report for PCT/US11/21758; Jul. 7, 2011, Rapiscan Systems Inc.
International Search Report for PCT/GB2009/000575, Apr. 7, 2010, Rapiscan Security Products Inc.
International Search Report for PCT/GB2004/001747, Aug. 10, 2004, CXR Ltd.
International Search Report for PCT/US2007/005444, Oct. 29, 2007, Telesecurity Sciences, Inc.
International Search Report for PCT/US2006/11492, Oct. 11, 2007, United Technologies Corporation.
Sun Olapiriyakul and Sanchoy Das, Design and analysis of a two-stage security screening and inspection system, Journal of Air Transport Management, vol. 13, Issue 2, Mar. 2007, pp. 67-74.

(56) References Cited

OTHER PUBLICATIONS

European Patent Office, International Search Report, International Application No. PCT/US99/28266, dated Sep. 6, 2000, 3 pages.
International Search Report, PCT/US2007/066936; dated: Sep. 30, 2008, 5 pages.
International Search Report, PCT/US1998/18642, dated Jul. 7, 1999, 4 pages.
International Search Report, PCT/US1999/028035, dated Sep. 15, 2000, 6 pages.
Written Opinion of the International Searching Authority, PCT/US2007/066936, dated Sep. 30, 2008, 7 pages.
Office Action dated Mar. 26, 2015 for U.S. Appl. No. 14/556,927.
Office Action dated Sep. 30, 2015 for U.S. Appl. No. 14/556,927.
International Search Report and Written Opinion for PCT/US2010/041757, Oct. 12, 2010.
Chou, C, "Fourier coded-aperture imaging in nuclear medicine", IEEE Proc. Sci. Meas. Technol., vol. 141. No. 3, May 1994, pp. 179-184.
European Patent Office Summons to attend oral proceedings pursuant to Rule 115{1) EPC, Application No. 05743513.3-2204/1733213, dated May 6, 2009, 3 pages.
European Patent Office, International Search Report and Written Opinion of the International Searching Authority, PCT/US2005/011382, Oct. 21, 2005.
International Search Report for PCT/US13/24191, Rapiscan Systems Inc., mailed on Jun. 25, 2013.
Notice of Allowance dated Feb. 12, 2015 for U.S. Appl. No. 13/756,211.
Search and Examination Report for Application No. GB1420349.1, dated Nov. 26, 2014.
Office Action dated Dec. 10, 2012 for U.S. Appl. No. 12/959,356.
Notice of Allowance dated May 5, 2015 for U.S. Appl. No. 14/047,477.
Office Action dated Apr. 28, 2015 for U.S. Appl. No. 14/454,295.
Office Action dated Sep. 1, 2015 for U.S. Appl. No. 14/454,295.
Patent Examination Report No. 1 for Australian Patent Application No. 2013215064, Oct. 13, 2014.
Supplementary Partial European Search Report for EP13743168, completed on Nov. 24, 2015.
First Office Action for Mexican Patent Application No. 2014009412, dated Oct. 22, 2015.
First Office Action for Chinese Patent Application No. 201380014384.6, dated Dec. 9, 2015.
Notice of Allowance dated Jun. 8, 2016 for U.S. Appl. No. 14/454,295.
Office Action dated Mar. 6, 2016 for U.S. Appl. No. 13/368,202.
Supplementary European Search Report for EP14746140, dated Aug. 12, 2016.

\* cited by examiner

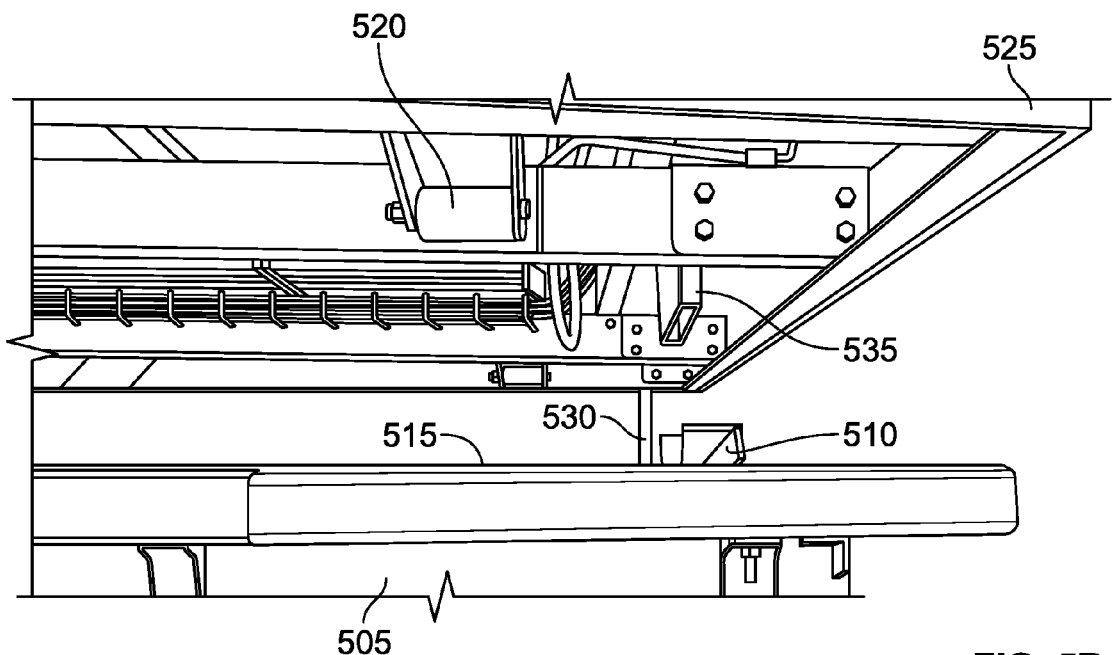
FIG. 5B
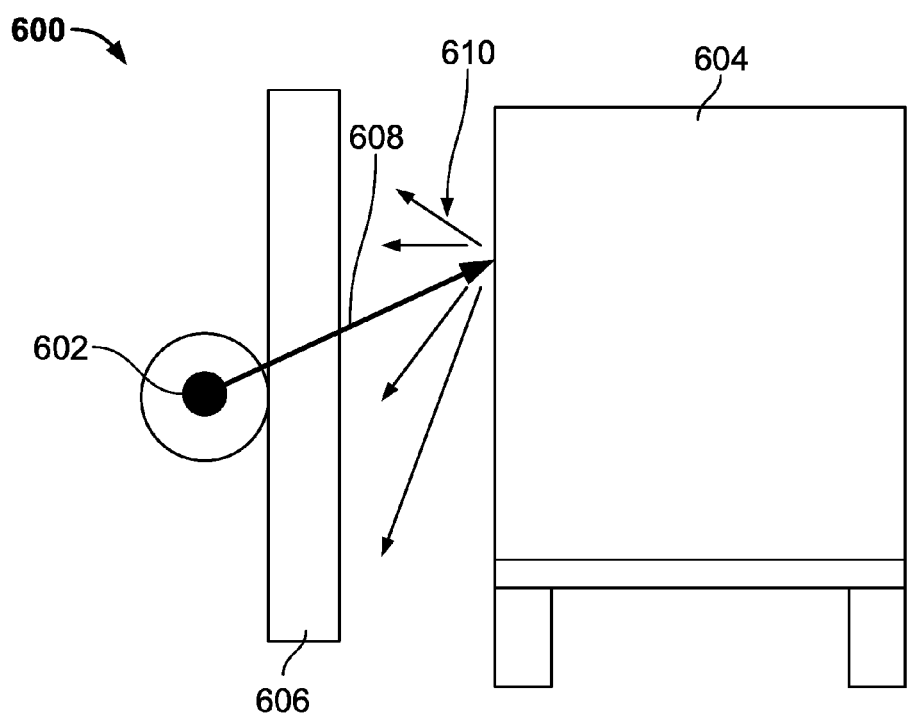
PRIOR ART  FIG. 6

PORTABLE SECURITY INSPECTION SYSTEM

CROSS-REFERENCE

The present application relies upon U.S. Provisional Patent Application No. 61/759,211 entitled "Portable Security Inspection System" and filed on Jan. 31, 2013.

FIELD

The present specification generally relates to portable inspection systems. More particularly, the present specification relates to a portable integrated X-ray inspection system that can be deployed at a plurality of surveillance locations, for performing a comprehensive security check of passing vehicles and cargo at various heights.

BACKGROUND

Trade fraud, smuggling and terrorism have increased the need for various non-intrusive inspection systems in applications ranging from curb-side inspection of parked vehicles to scanning in congested or high-traffic ports because transportation systems, which efficiently provide for the movement of commodities across borders, also provide opportunities for the inclusion of contraband items such as weapons, explosives, illicit drugs and precious metals. The term port, while generally accepted as referring to a seaport, also applies to a land border crossing or any port of entry.

X-ray systems are used for medical, industrial and security inspection purposes because they can cost-effectively generate images of internal spaces not visible to the human eye. Materials exposed to X-ray (or any other type of) radiation absorb differing amounts of X-ray radiation and, therefore, attenuate an X-ray beam to varying degrees, resulting in a transmitted or backscattered level of radiation that is characteristic of the material. The attenuated or backscattered radiation can be used to generate a useful depiction of the contents of the irradiated object. A typical single energy X-ray configuration used in security inspection equipment may have a fan-shaped or scanning X-ray beam that is transmitted through or backscattered by the object inspected. The absorption or backscattering of X-rays is measured by detectors after the beam has passed through the object and an image is produced of its contents and presented to an operator.

With limited space and a need to expand, finding suitable space to accommodate additional inspection facilities along the normal process route remains difficult. Additionally, selected locations are not necessarily permanent enough for port operators to commit to the long term installation of inspection equipment. Moreover, systems incorporating high-energy X-ray sources, or linear accelerators (LINAC), require either a major investment in shielding material (generally in the form of concrete formations or buildings) or the use of exclusion zones (dead space) around the building itself. In either case, the building footprint requirement is generally too significant depending upon the size of cargo containers to be inspected.

A mobile inspection system offers an appropriate solution to the need for flexible, enhanced inspection capabilities. Because the system is relocatable and investment into a permanent building in which to accommodate the equipment is obviated, site allocation becomes less of an issue and introducing such a system becomes less disruptive. Also, a mobile inspection system provides operators, via higher throughput, with the ability to inspect a larger array of cargo, shipments, vehicles, and other containers.

Conventional inspection systems are disadvantageous in that they suffer from a lack of rigidity, are difficult to implement, and/or have smaller fields of vision. Specifically, conventional relocatable inspection systems generally comprise at least two booms, wherein one boom will contain a plurality of detectors and the other boom will contain at least one X-ray source. The detectors and X-ray source work in unison to scan the cargo on the moving vehicle. In conventional single boom relocatable inspection systems, the X-ray source is located on a truck or flatbed and the detectors on a boom structure extending outward from the truck. These systems are characterized by moving-scan-engine systems wherein the source-detector system moves with respect to a stationary object to be inspected. Also, the detectors and the source of radiation are either mounted on a moveable bed, boom or a vehicle such that they are integrally bound with the vehicle. This limits the flexibility of dismantling the entire system for optimum portability and adjustable deployment to accommodate a wide array of different sized cargo, shipments, vehicles, and other containers. As a result these systems can be complicated to deploy and pose several disadvantages and constraints.

Accordingly, there is need for improved inspection methods and systems that may be rapidly loaded over a truck or a trailer being pulled by any vehicle and transported to a surveillance location for rapid and facile deployment.

There is also need for a portable inspection system that does not require a specialized, expensive transportation vehicle in order to be transported to a surveillance site.

There is a further need for a portable inspection system that is light weight and may be rapidly deployed for inspection.

SUMMARY

The present specification generally provides a portable non-invasive security inspection system that is easily and rapidly deployed.

In addition, the present specification provides a radiation inspection arrangement designed to be easily encased in a container, such as but not limited to, a reinforced box which may be transported to a plurality of locations requiring surveillance.

The present specification also provides a radiation inspection arrangement designed to be easily encased in a container which may be transported to a plurality of surveillance locations by loading on a truck or a trailer being pulled by any transportation vehicle.

The present specification also provides a radiation inspection arrangement designed to be easily encased in a container that does not require any specialized vehicle for transportation to a surveillance site.

The present specification also provides a portable radiation inspection system which is lightweight and may easily be deployed at a surveillance location for inspecting passing vehicles and cargo.

The present specification also provides a portable radiation inspection system which is lightweight and may easily be deployed at a surveillance location for inspecting people and their possessions.

The present specification also provides a portable radiation inspection system that can be easily deployed at various heights allowing for inspection of cars, vans, and trucks.

In one embodiment, the present specification includes a radiation inspection system comprising at least one or more types of radiation source(s) and detector assemblies.

In one embodiment, the portable inspection system is a backscatter X-ray inspection system comprising a backscatter X-ray source and detection assembly.

In one embodiment, the present specification describes an inspection system for screening an object under inspection comprising: a container with four walls, a ceiling and a base that defines an enclosed volume; at least one radiation source positioned within said enclosed volume, wherein emissions from said radiation source define a field of view; at least one detector array positioned within said enclosed volume or physically attached to said container; and a plurality of legs attached to said container at each of four corners, wherein said plurality of legs are extendable to at least one height position from ground level and wherein said at least one height position is determined using a plurality of data.

In one embodiment, said plurality of data includes dimensions of the objects under inspection, desired inspection area, detector array configuration, desired field of view, X-ray source type, X-ray source configuration, and constraining structures or the presence of people.

In one embodiment, said container further comprises vertical recesses at each of four corners to accommodate said plurality of legs.

In one embodiment, in a stowed position, said plurality of legs rest within said vertical recesses to lie at least partially embedded with respect to the vertical walls of said container.

In one embodiment, in a stowed position, said container rests on a trailer portion of a transportation vehicle.

In one embodiment, in a deployed position at a surveillance site, at least one of said plurality of legs is first extended horizontally outwards from said four corners of the container and subsequently vertically downwards so that said plurality of legs are in contact with the ground thereby lifting said container off from the trailer portion.

In one embodiment, said trailer portion is driven away from the container once said plurality of legs are in contact with the ground and said inspection system is in a fully deployed position. In one embodiment, to transport said container from said surveillance site the trailer portion is driven beneath said container and said plurality of legs are vertically retracted to lower and stow said container on said trailer portion.

In one embodiment, said at least one source and said at least one detector array are configured to generate scan information from an object under inspection.

In one embodiment, once deployed, said legs are telescopically retracted such that said container is in contact with the ground, two of said four walls of said container are folded down.

In one embodiment, once two of said four walls of said container are folded down, said ceiling is optionally vertically extended upwards if required by the scanning application to form a drive thought portal at said surveillance site.

In one embodiment, said at least one source and said at least one detector array are configured to generate multi-view scan images of an object under inspection.

In another embodiment, the present specification describes an inspection system for deployment at a surveillance site, comprising: a container with four walls, a ceiling and a base that defines an enclosed volume, wherein said container is stowed on a trailer portion of a transportation vehicle; at least one radiation source positioned within said enclosed volume, wherein emissions from said radiation source define a field of view; at least one detector array positioned within said enclosed volume or physically attached to said container; and a plurality of legs attached to said container at each of four corners, wherein said plurality of legs are extendable by first moving said at least one of said plurality of legs horizontally outwards from said container and subsequently moving said plurality of legs vertically downwards so that the legs are in contact with the ground, thereby lifting said container off of said trailer portion.

In one embodiment, a height of said container above the ground is adjustable using a telescopic motion of said plurality of legs. In one embodiment, the height of said container above the ground is determined using a plurality of data wherein said plurality of data includes dimensions of the objects under inspection, desired inspection area, detector array configuration, desired field of view, X-ray source type, X-ray source configuration, and constraining structures or the presence of people.

In yet another embodiment, the present specification describes a method of deploying an inspection system comprising: a container with four walls, a ceiling and a base that defines an enclosed volume, wherein said container is stowed on a trailer portion of a transportation vehicle; at least one radiation source positioned within said enclosed volume, wherein emissions from said radiation source define a field of view; at least one detector array positioned within said enclosed volume or physically attached to said container; and a plurality of legs attached to said container at each of four corners of said container, the method comprising: extending at least one of said plurality of legs horizontally outwards from said four corners of said container; extending said plurality of legs vertically downwards so that said plurality of legs is in contact with the ground at a surveillance site; continuing to extend said plurality of legs vertically downwards to enable said container to be lifted off from the trailer portion and be supported fully on said plurality of legs at said surveillance site; and driving said trailer portion away from said surveillance site.

In one embodiment, a height of said plurality of legs is adjusted to accommodate a plurality of scanning heights. In one embodiment, the height of said container above the ground is determined using a plurality of data wherein said plurality of data includes dimensions of the objects under inspection, desired inspection area, detector array configuration, desired field of view, X-ray source type, X-ray source configuration, and/or constraining structures or the presence of people.

In one embodiment, said plurality of legs is fully retracted such that said container is positioned at ground level, two of said four walls of said container are folded down and said ceiling is optionally vertically extended upwards to form a drive thought portal at said surveillance site.

The aforementioned and other embodiments of the present shall be described in greater depth in the drawings and detailed description provided.

BRIEF DESCRIPTION OF THE DRAWINGS

These and other features and advantages of the present specification will be further appreciated, as they become better understood by reference to the detailed description when considered in connection with the accompanying drawings:

FIG. 5B illustrates the container being received over the equipped trailer chassis;

FIG. 6 is a schematic representation of an X-ray source detector assembly known in the art that may be used in the X-ray inspection system, in accordance with an embodiment of the present specification;

DETAILED DESCRIPTION

The present specification describes a portable radiation inspection system. In various embodiments the portable inspection system is designed to be easily encased in a container, such as, but not limited to as a reinforced box, which may be transported to a plurality of locations requiring surveillance. The inspection system in the box may be rapidly deployed at a surveillance location, without requiring complex set up procedures. Further, in various embodiments, both the inspection system and the encasing box are made of lightweight components, allowing transportation of the same by using any suitable vehicle such as a truck or a trailer, and easy deployment at a surveillance site. In various embodiments the portable inspection system is used to scan objects such as passing vehicles or cargo positioned outside the encasing box with radiation.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present specification.

It should be noted herein that although the system described in the present specification, refers to the use of X-ray radiation, any suitable radiation source or combination thereof may be employed with the present invention. Examples of other suitable radiation sources comprise Gamma-ray, microwave, optical, radio frequency, millimeter wave, terahertz, infra-red and ultrasound radiations.

As would be apparent to persons of skill in the art, the cost and complexity of a suitable transportation vehicle is a limitation in the use of portable radiation inspection systems in remote locations. The present specification provides a self-contained inspection system which may be transported to a surveillance site without requiring the use of any specialized and expensive vehicles for transportation, and may be easily deployed there, ready to start automated inspection of passing vehicles and cargo.

Figure 1:
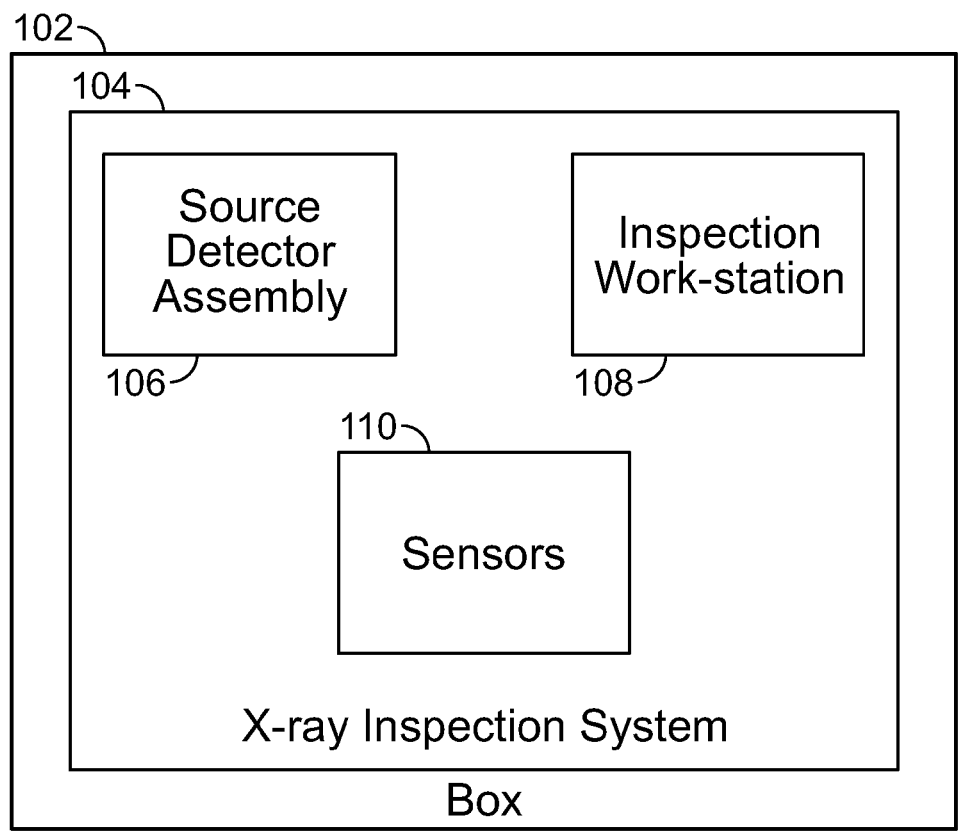
FIG. 1 is a block diagram of an exemplary X-ray inspection system encased in a box, in accordance with an embodiment of the present specification.

FIG. 1 is a block diagram showing an exemplary inspection system encased in a box, in accordance with an embodiment of the present specification. In various embodiments, the inspection system 102 is encased in a container, such as a box 104, having four sides, a floor and ceiling, and comprises a source-detector assembly 106 for obtaining a radiographic image of an object being inspected, and an inspection workstation 108. Image data from the source-detector assembly 104 is transferred to the inspection workstation 108 which may be located adjacent to the source-detector assembly 106, within the container, or remotely as required in the application. The inspection workstation 108 may be located inside an armored vehicle, in an existing building, in a temporary structure or within the inspection system 102. The inspection workstation is in data communication with the inspection system using any form of wired or wireless communication.

In various embodiments, the portable radiation inspection system of the present specification comprises an X-ray source and a plurality of detectors for obtaining a radiographic image of an object being inspected.

In an embodiment, the X-ray inspection system comprises high energy inspection equipment based on transmission imaging with X-ray radiation generated by a linear accelerator with typical beam quality of 1 MeV to 9 MeV. Such systems are very effective at probing the structure and shape of relatively high atomic number articles.

In an embodiment, the X-ray inspection system 102 also comprises one or more sensors 110 for analysis of one or more parameters of passing vehicles and cargo. Examples of sensors 110 include photographic devices, video cameras, thermal cameras, Infrared (IR) cameras, trace chemical detection equipment, radio frequency (RF) monitoring devices, RF jamming devices, automated number plate capture systems and automated container code capture systems. In an embodiment, ancillary data, including image, video, graphic, temperature, heat, chemical, communication signals, or other data, obtained via the sensors 110 is also transferred to the inspection workstation 108 and presented in a graphical form for system inspector's review. In one embodiment, ancillary data is advantageously combined to produce an overall consolidated threat report for the system inspector.

Figure 2A:
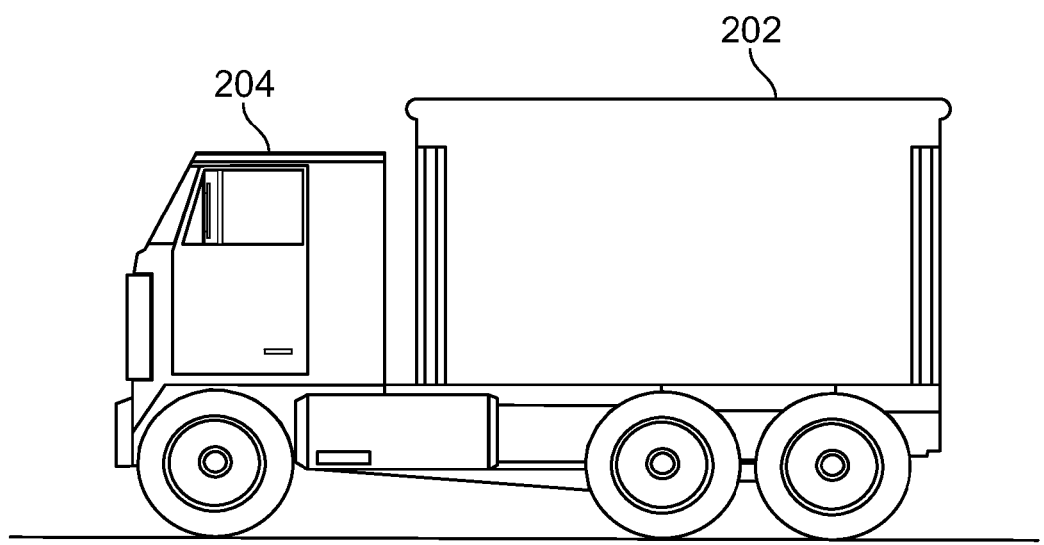
FIG. 2A illustrates the X-ray inspection system encased in a box loaded on a vehicle for transportation, in accordance with an embodiment of the present specification.

In various embodiments, the portable X-ray inspection system of the present specification can be used with any vehicle that allows for the system to be rapidly re-locatable and easily transportable. FIG. 2A illustrates the X-ray inspection system of the present specification encased in a box 202 which is capable of being transported on the back of a vehicle 204 at highway speeds from one surveillance site to another. In an embodiment, the weight of the X-ray inspection system encased in the box 202 ranges from 100 kilograms to 4500 kilograms depending on site-specific sensor configuration and integrated shielding requirements.

Figure 2B:
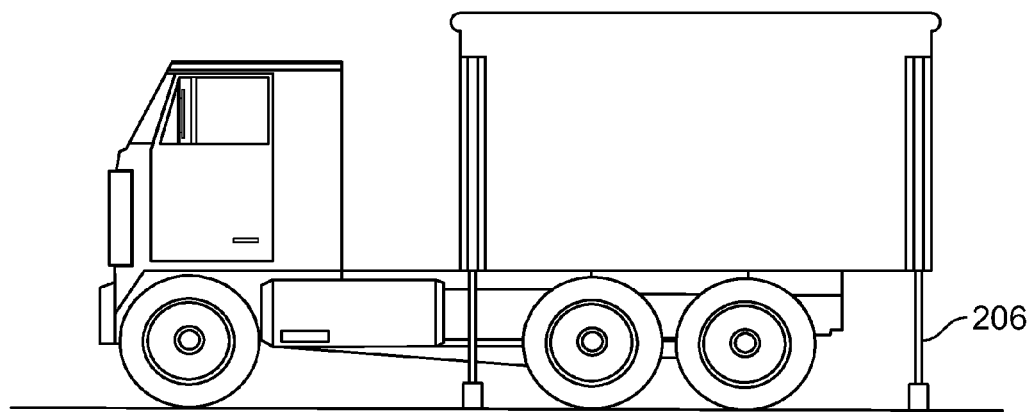
FIG. 2B illustrates the X-ray inspection system encased in a box comprising extendable legs in accordance with an embodiment of the present specification.

FIG. 2B illustrates the X-ray inspection system encased in a box 202 comprising extendable legs 206 which may be drawn down to ground level to support the full weight of the X-ray inspection system. The extendable legs 206 are used to lift the X-ray inspection system up and off the back of the transport vehicle 204.

In various embodiments a plurality of extendable leg designs may be implemented, including any form of propelled movement such as mechanical, hydraulic and pneumatic designs, and all such designs are covered in the scope of this specification.

In an embodiment, the height of the extendable legs 206 may be adjusted causing the X-ray inspection system to be held at a desired height above the ground facilitating inspection of passing vehicles and cargo. In an embodiment, in addition to establishing an optimum height of the X-ray inspection system with respect to objects under inspection, the field of view of the X-ray inspection system (in a vertical plane) may also be adjusted for covering a required field of view while minimizing overall radiation exposure to the environment. In one embodiment, the field of view is adjusted manually by first using a multi-point switch, such as a three-position switch, to set the required height of the X-ray inspection system and then actuating a button (such as a raise or lower button) to affect movement of the inspection system to the earlier set height. In another embodiment, the field of view is adjusted automatically based on video analysis of an approaching object to be inspected.

In one embodiment, a controller is programmed to determine an optimum height of the extendable legs 206 based upon a plurality of data, including dimensions of the objects under inspection, desired inspection area, detector array configuration, desired field of view, X-ray source type, X-ray source configuration, and/or constraining structures or the presence of people. It should be appreciated that the controller may be used to control the height of any platform or supporting structure, if legs 206 are not specifically used. It should be understood by those of ordinary skill in the art that, depending upon the object under inspection and the checkpoint requirements, the plurality of data can be manipulated accordingly.

Once a scanning operation of X-ray inspection system at a surveillance site is completed, the X-ray inspection system encased in a box is re-loaded onto the back of a transportation vehicle by using the extendable legs and is rapidly transported to another surveillance site. In an embodiment, the X-ray inspection system may be towed from one surveillance site to another on a trailer behind a general purpose vehicle. The deployment and reload of the inspection system of the present invention is described in detail with respect to FIGS. 4A to 4Q below.

Figure 3:
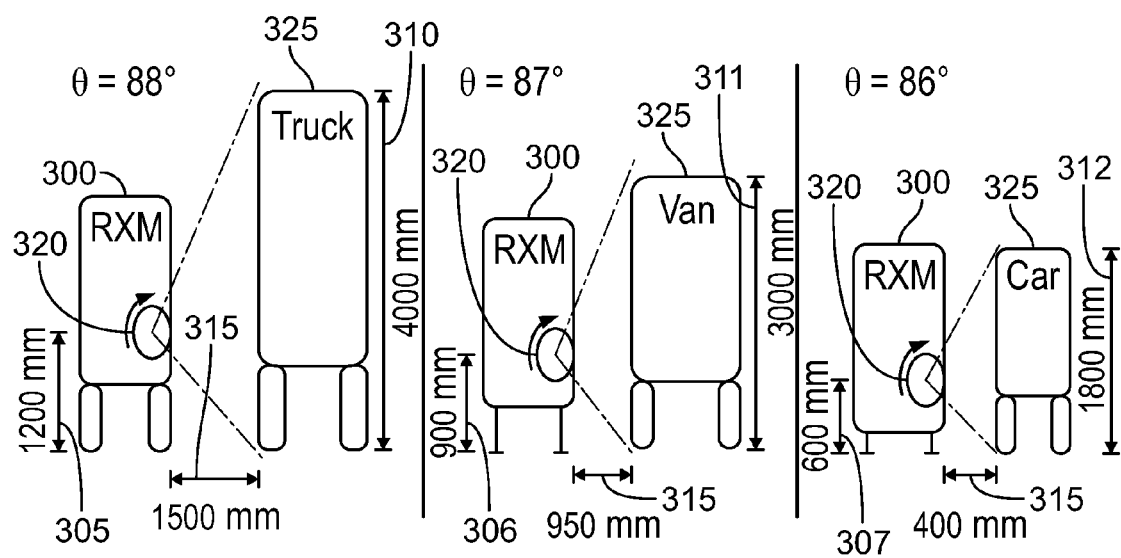
FIG. 3 illustrates a plurality of exemplary container heights to scan vehicles of differing heights.

FIG. 3 illustrates inspection container 300 positioned at different heights 305, 306, 307 above the ground to scan vehicles or objects 325 having differing heights 310, 311, 312. Further, inspection container 300 is positioned, in one embodiment, at a distance 315 from the object or vehicle under inspection. Still further, in one embodiment, inspection container 300 affords a field of view 320 of varying degrees depending upon the vehicle or object to be inspected. In one embodiment, where vehicle 325 is a truck having a height 310 of approximately 4000 mm, inspection container 300 is positioned at a height 305 of 1200 mm from the ground. Further, inspection container is placed at a distance 315 of 1500 mm from the vehicle 307. This configuration affords an overall field of view 320 of 88 degrees.

In another embodiment, where vehicle 325 is a van having a height 311 of approximately 3000 mm, inspection container 300 is positioned at a height 306 of 900 mm from the ground. Further, inspection container is placed at a distance 315 of 950 mm from the vehicle 307. This configuration affords an overall field of view 320 of 87 degrees.

In yet another embodiment, where vehicle 325 is a car having a height 312 of approximately 1800 mm, inspection container 300 is positioned at a height 307 of 600 mm from the ground. Further, inspection container is placed at a distance 315 of 400 mm from the vehicle 307. This configuration affords an overall field of view 320 of 86 degrees.

The examples above are exemplary and it should be understood to those of skill in the art that adjustments may be made to achieve the scanning objectives of the present specification.

Figure 4A:
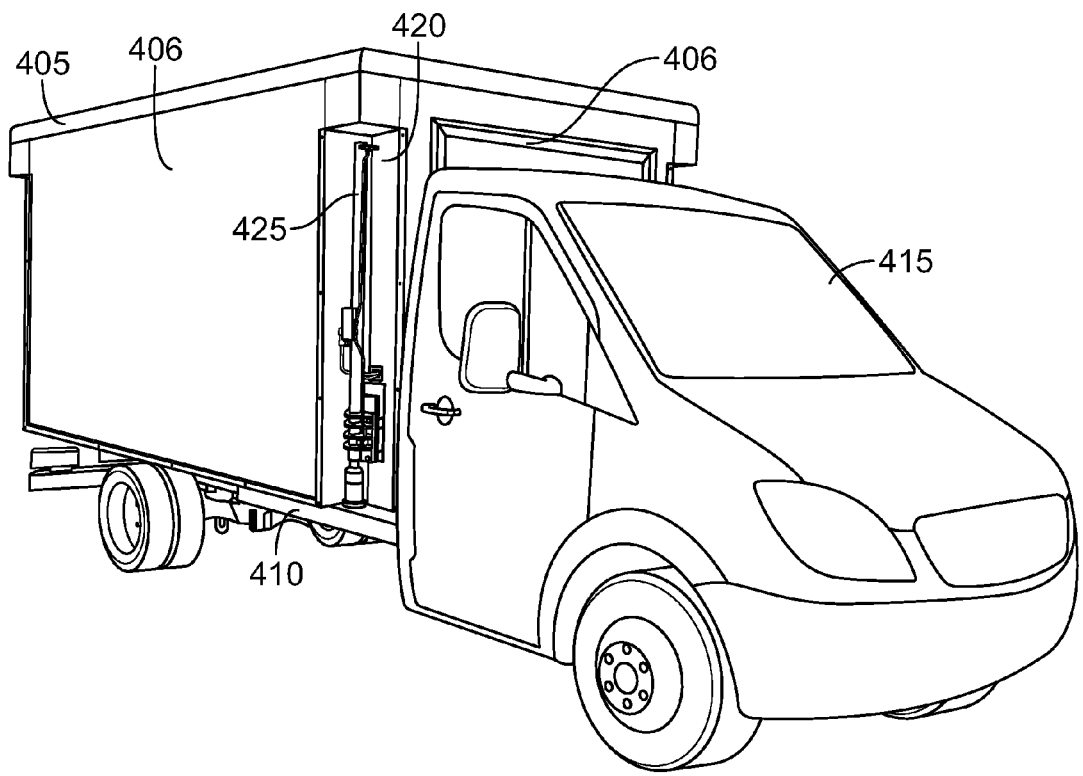
FIG. 4A is a perspective view of the X-ray inspection system encased in a container comprising extendable legs and stowed on a trailer.
Figure 4B:
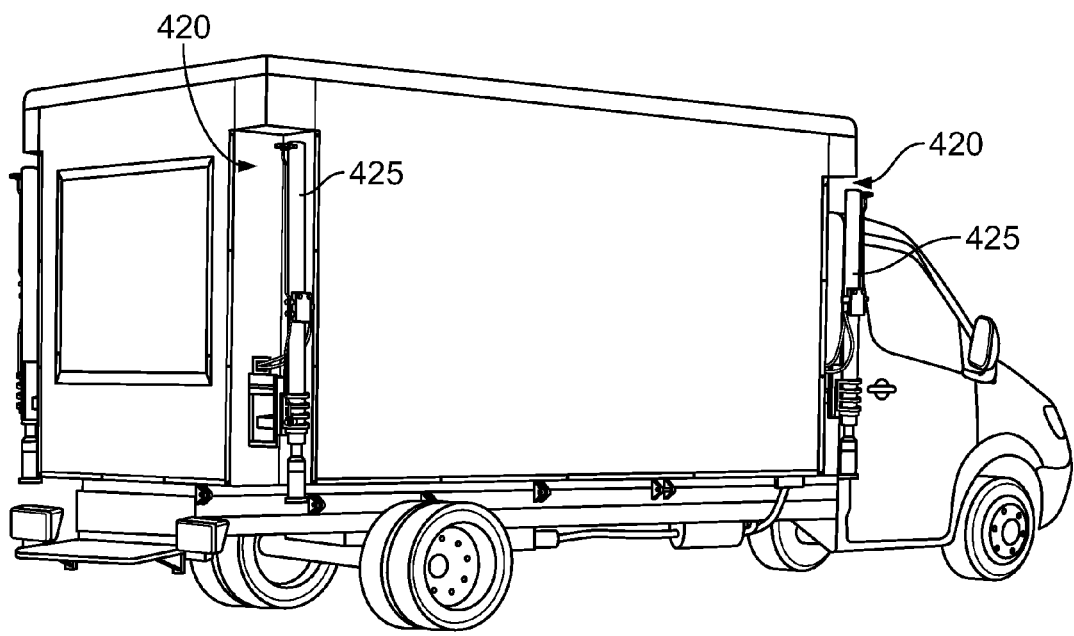
FIG. 4B illustrates the legs being horizontally extended out from the container.
Figure 4C:
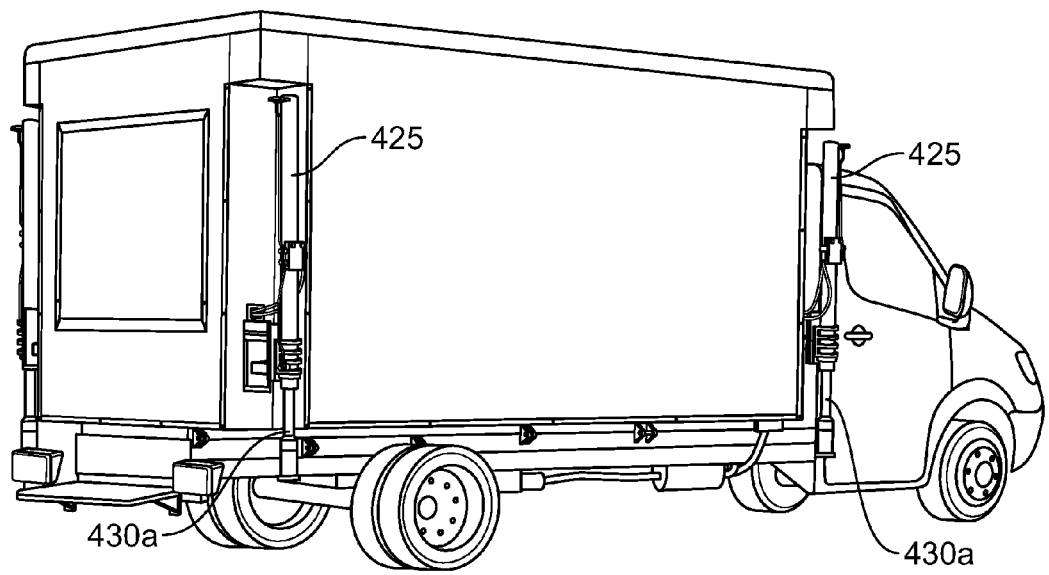
FIG. 4C illustrates a first intermediate vertically extended leg-position.
Figure 4D:
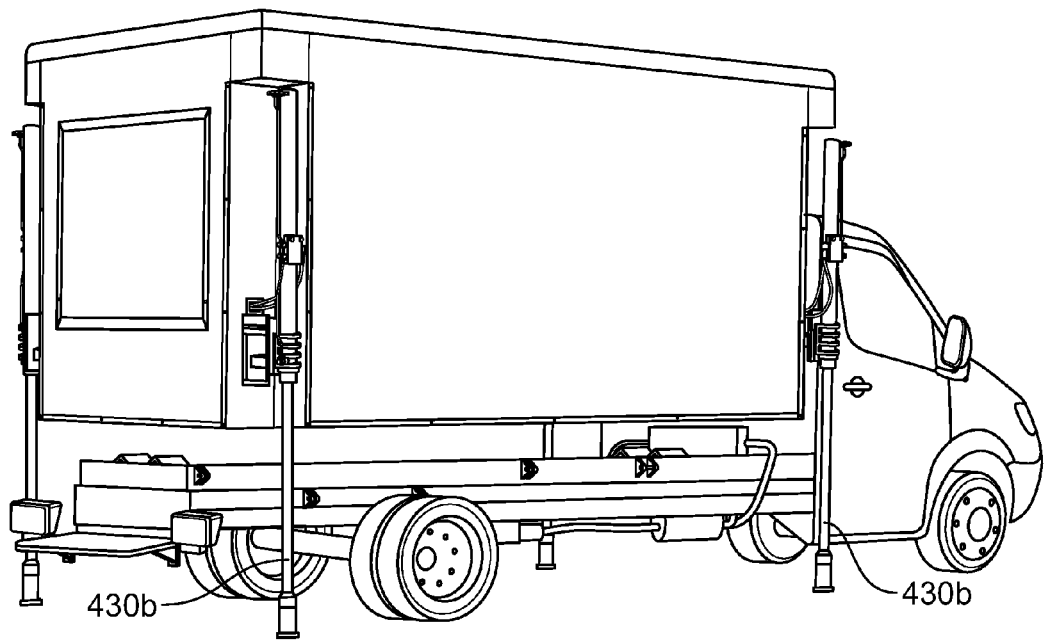
FIG. 4D illustrates a second intermediate vertically extended leg-position.
Figure 4E:
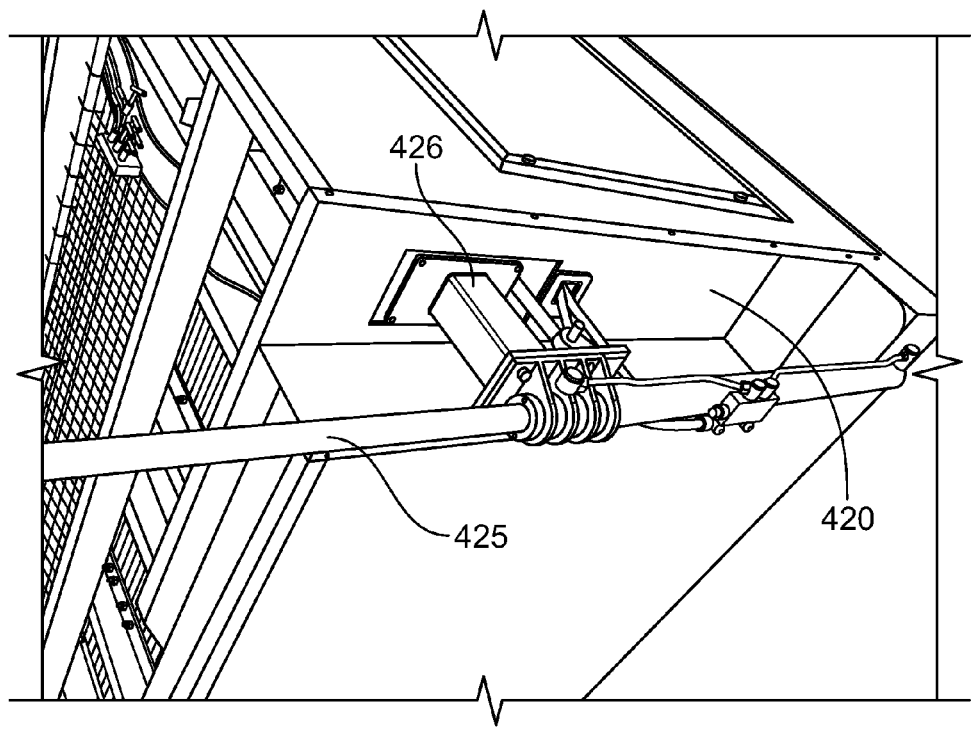
FIG. 4E is a close-up view of the leg being horizontally and vertically extended from the container.
Figure 4F:
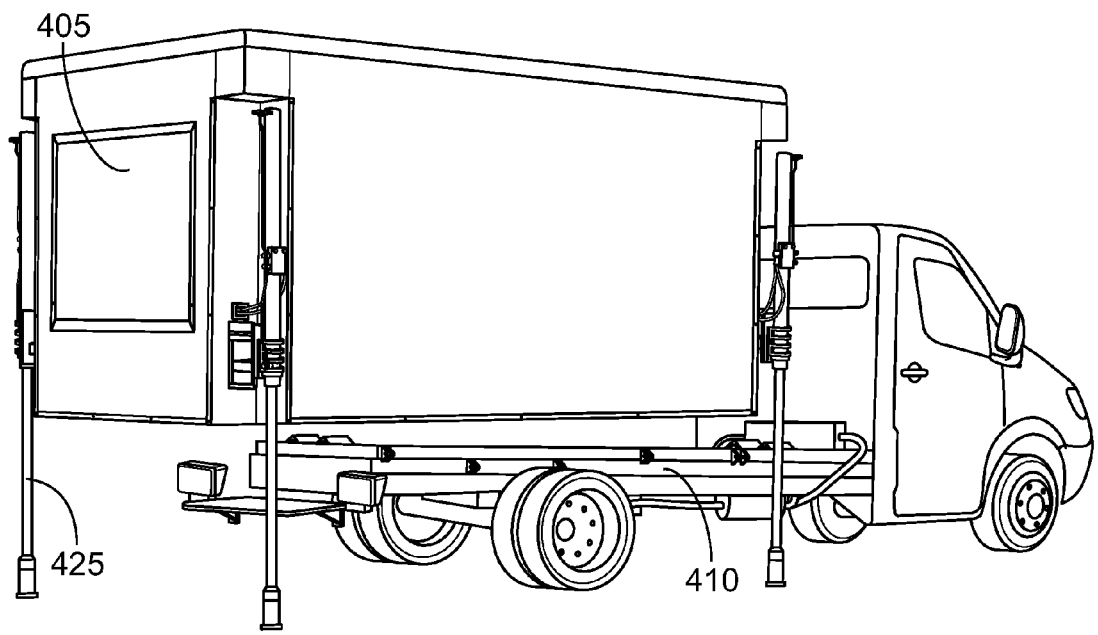
FIG. 4F illustrates the legs being vertically extended enough to lift the container off from the trailer.
Figure 4G:
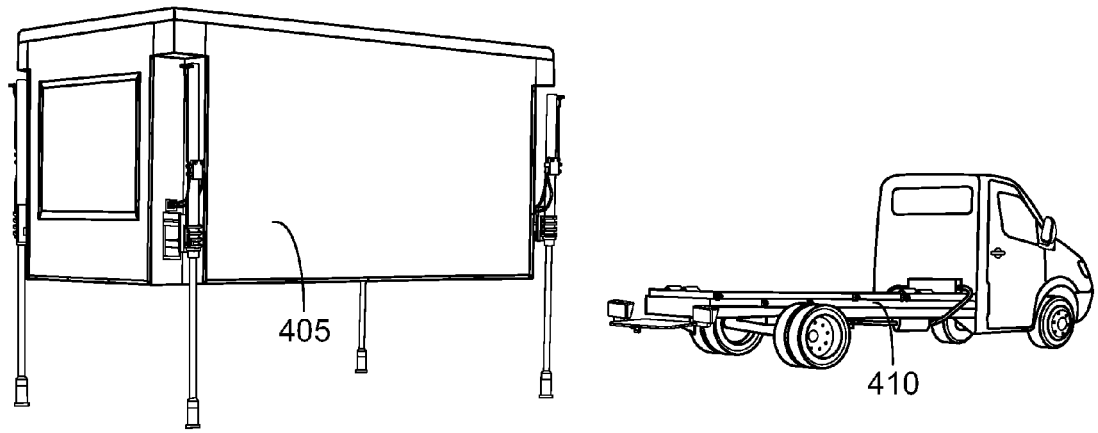
FIG. 4G illustrates the container being deployed on its four extended legs while the supporting trailer is moved away from beneath the container.
Figure 4H:
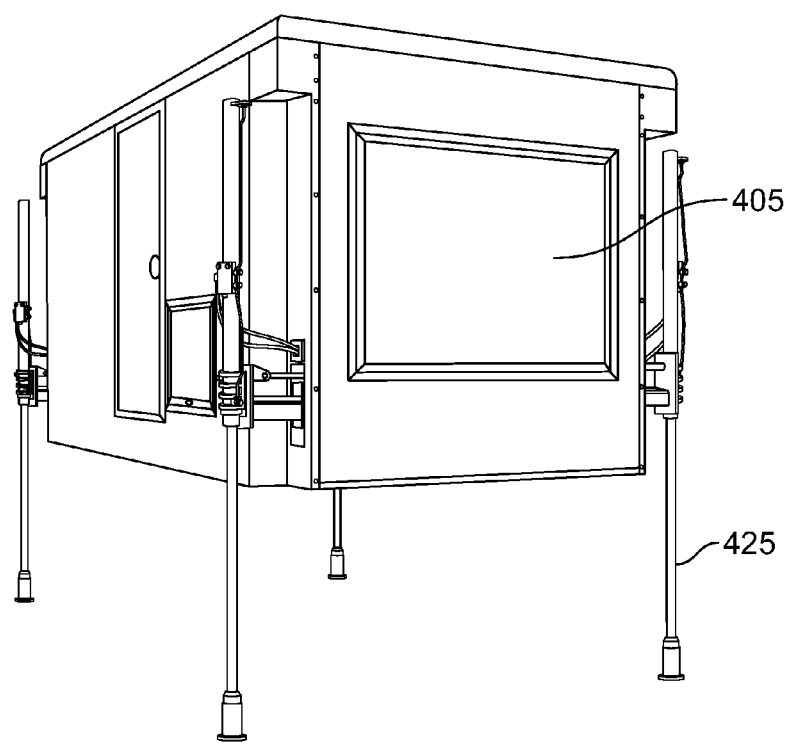
FIG. 4H illustrates the container being deployed on its four extended legs.
Figure 4I:
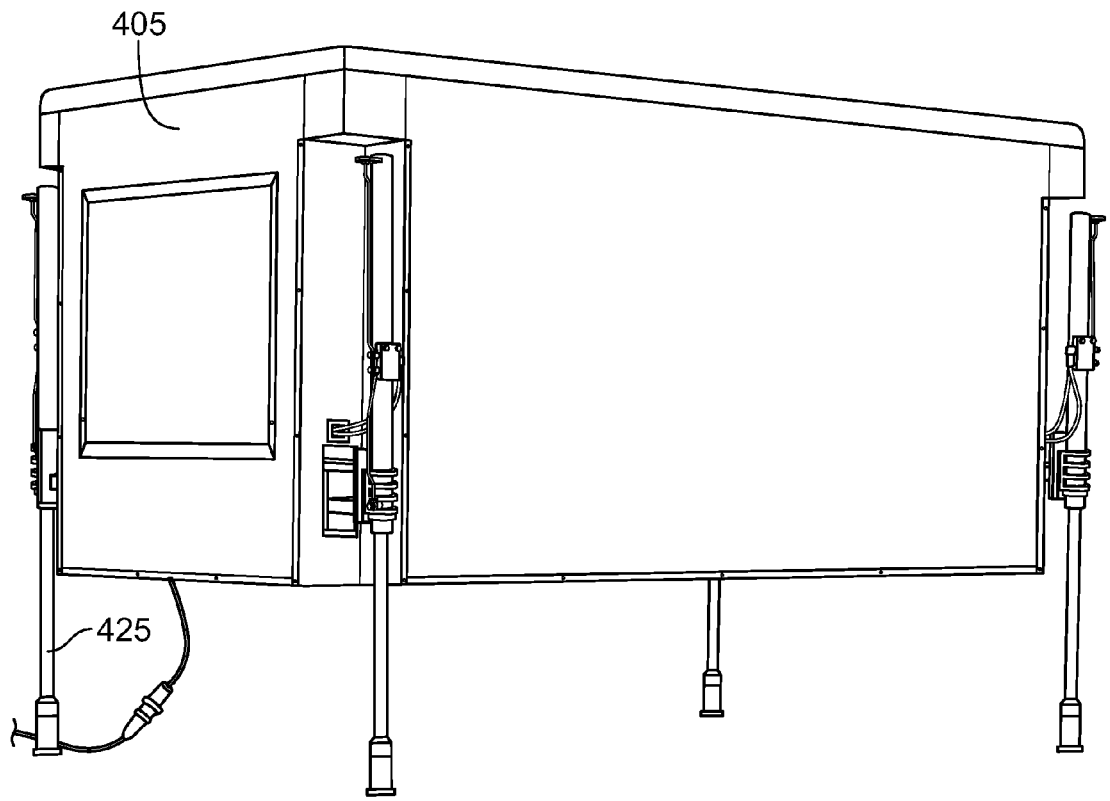
FIG. 4I illustrates the container being deployed at a first exemplary height above the ground.
Figure 4J:
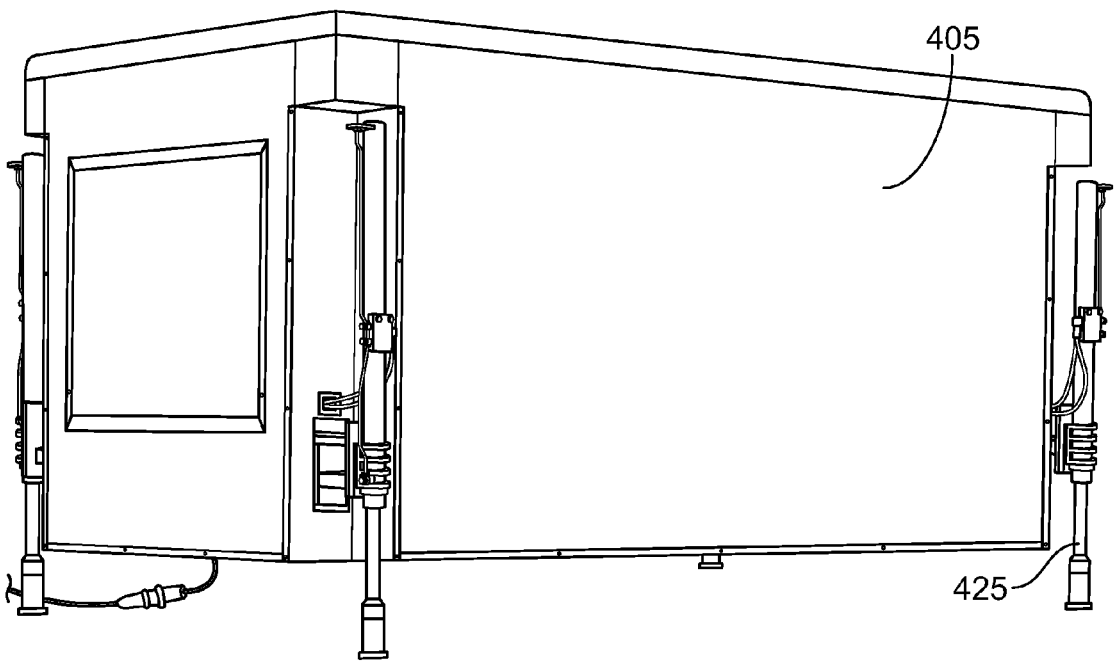
FIG. 4J illustrates the container being deployed at a second exemplary height above the ground.
Figure 4K:
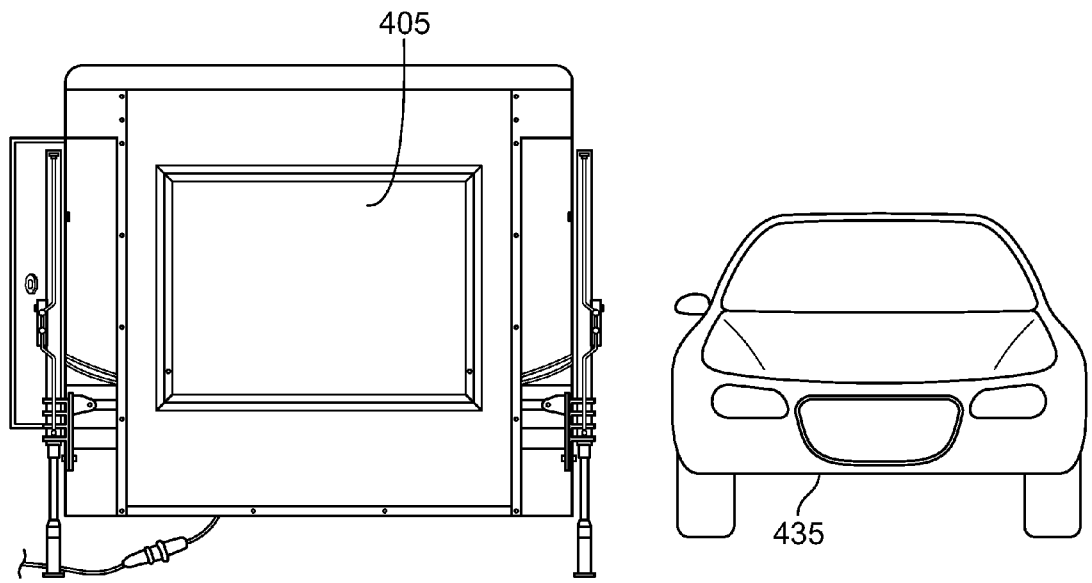
FIG. 4K illustrates scanning of a passing vehicle using the deployed container encasing the X-ray inspection system.
Figure 4L:
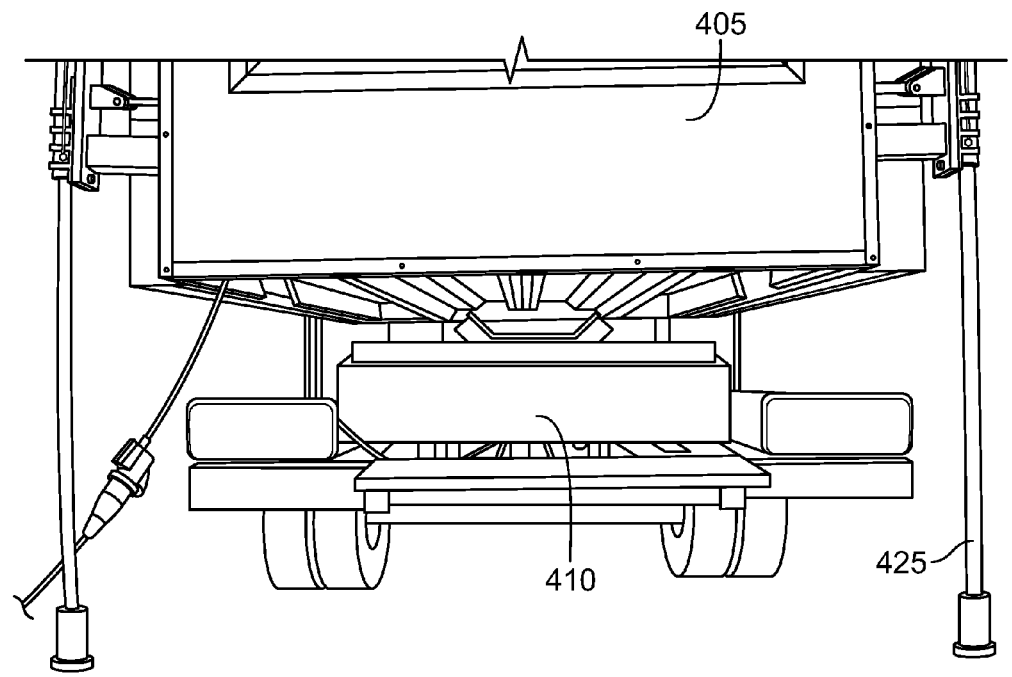
FIG. 4L illustrates the positioning of the trailer beneath the deployed container to begin reloading of the container onto the trailer.
Figure 4M:
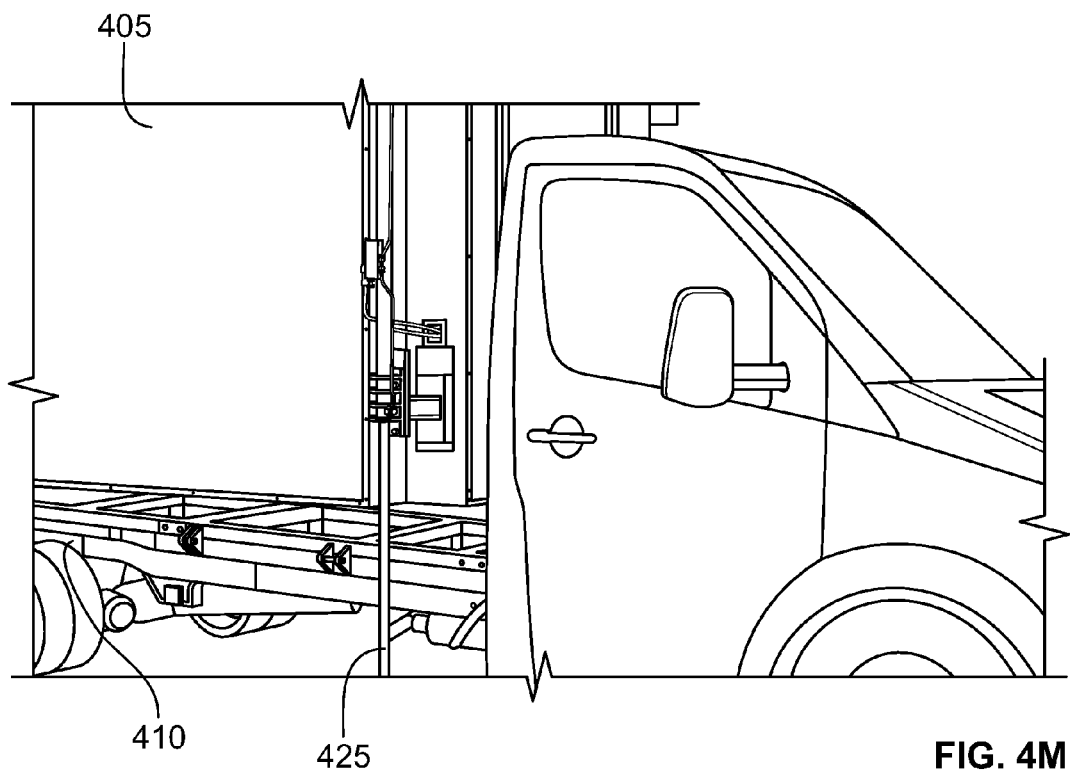
FIG. 4M illustrates the container being lowered onto the trailer.
Figure 4N:
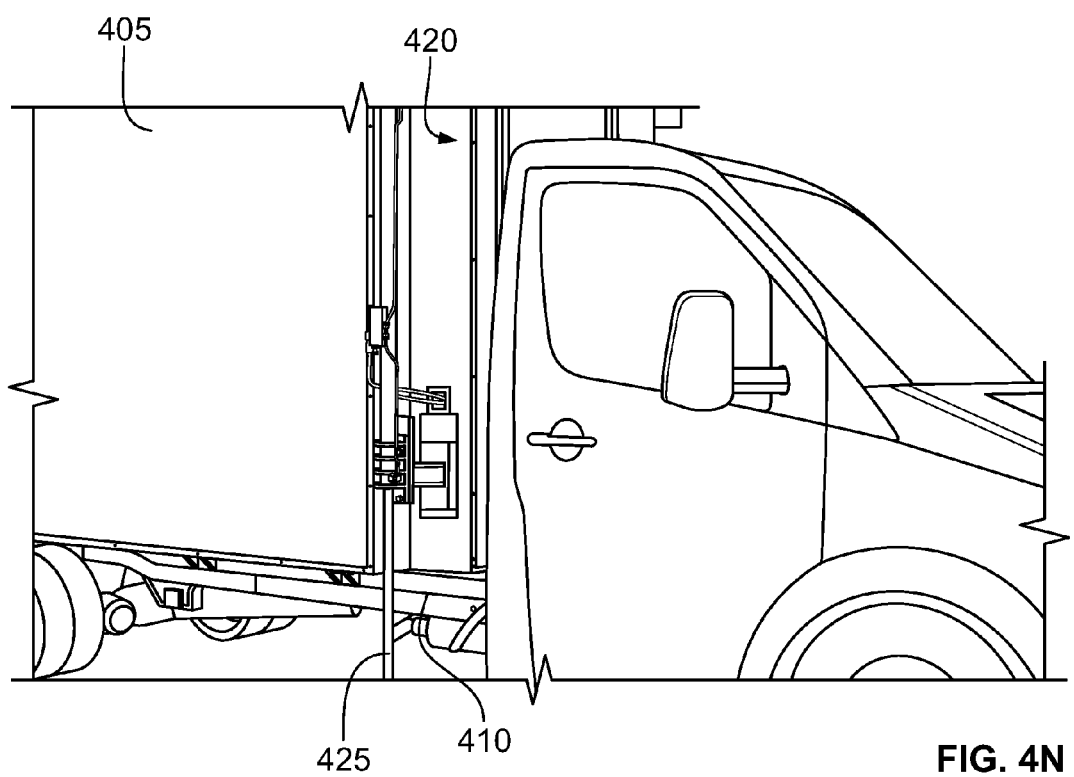
FIG. 4N illustrates the container stowed onto the trailer.
Figure 4O:
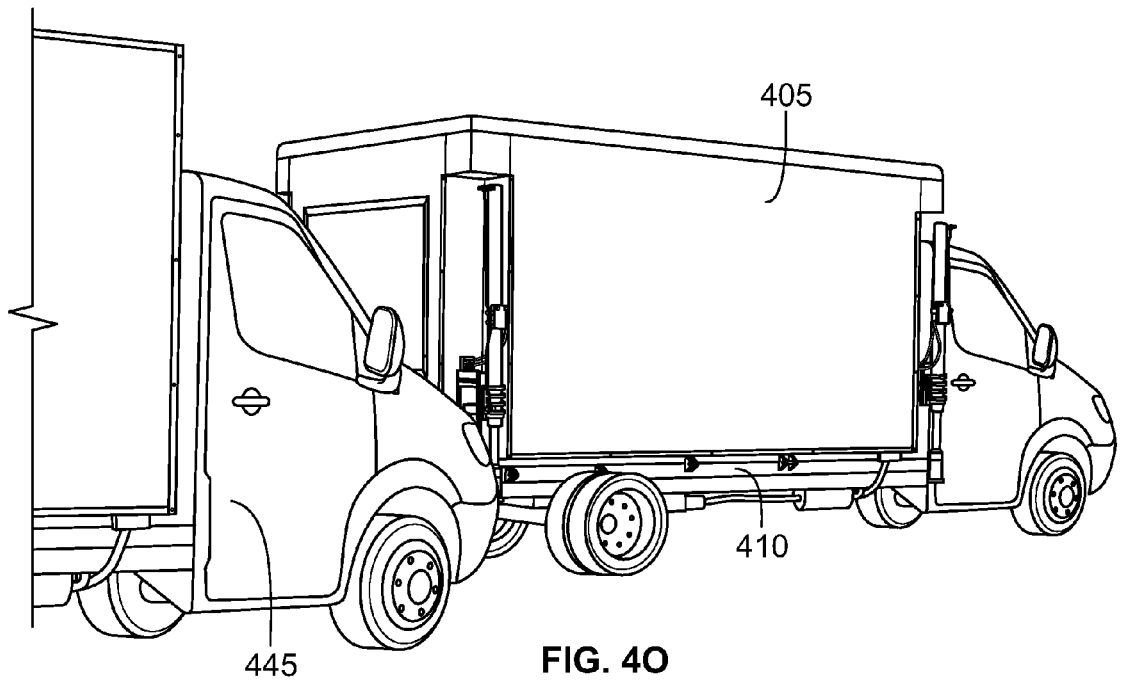
FIG. 4O illustrates the X-ray inspection system encased in the container stowed on the stationery trailer being used to scan a passing vehicle.

FIGS. 4A through 4O show perspective in-theater views of the inspection system of the present specification, encased in a container /compartment such as a box, being deployed from a transportation vehicle onto a surveillance site and then reloaded or stowed back onto the transportation vehicle.

FIG. 4A illustrates the X-ray inspection system of the present specification, encased in container 405, and stowed on a trailer portion 410 of a transportation vehicle 415. In one embodiment, transportation vehicle 415 is a truck that is suitable for transport on surface streets or the highway, at regular speeds. In accordance with an embodiment of the present invention, the container 405 comprises four vertical walls 406, forming substantially a rectangular box. Further, container 405 comprises four vertical recesses 420 one on each of four corners of the container 405. Each vertical recess 420 accommodates a leg 425 that when in a stowed position, the legs 425 rest within the vertical recesses 420 such that they lie flush or slightly embedded with respect to respective vertical walls 406 of the container 405.

Each leg 425, in a deployed position, can be extended horizontally away from its respective corner of the container 405 and can also be extended up and down vertically, in a telescoping manner, so as to set the height of the base of the container 405 at variable heights above ground level. For deployment at a surveillance site, at least one of the legs 425 are first extended horizontally outwards from their respective vertical recesses 420, as shown in FIG. 4B. It should be noted that it may not be required for all of the legs to extend horizontally and this is dependent upon the necessity of clearance for allowing the trailer wheels to pass through the legs. Thereafter, the legs 425 are extended vertically downwards as shown in a first intermediate vertically or telescopically extended leg-position 430a of FIG. 4C and a second intermediate vertically or telescopically extended leg-position 430b of FIG. 4D. As shown in FIG. 4D, in extended leg-position 430b the legs 425 touch the ground.

FIG. 4E is a close-up view illustrating a piston 426 in horizontally extended position thereby enabling horizontal extension of the leg 425 outwardly from the vertical recesses 420. The leg 425 is also visible as having been telescoped vertically downwards so that it is in a vertically extended leg-position, such as position 430b of FIG. 4D.

As shown in FIG. 4F, the legs 425 are further telescoped or extended vertically downwards, beyond leg-position 430b of FIG. 4D (wherein the legs 425 touched the ground), causing the container 405 to be raised and lifted off from the chassis of the trailer 410. Once the container 405 is positioned at an optimal height and all four legs 425 are touching the ground, the trailer 410 is towed away from beneath the container 405 as shown in FIG. 4G.

As a result, as shown in FIG. 4H, the container 405 is now deployed and standing on fully extended/telescoped legs 425 at a first height at the surveillance site. The height of the base of the container 405 above ground can now be adjusted, for scanning, by using the vertical telescopic movement of legs 425. FIG. 4I illustrates legs 425 in a second vertically refracted position to place the container 405 at a second height while FIG. 4J shows the legs 425 in a third vertically retracted position to place the container 405 at a third height. Persons of ordinary skill in the art should appreciate that once deployed on the ground the legs 425 can be retracted or extended vertically to respectively lower or raise the container 405 at varying distances above ground to accommodate different scanning heights. The first, second and third heights of the container 405 in FIGS. 4H through 4J correspond to container heights 305, 306, 307 of FIG. 3.

Once legs 425 are retracted or extended vertically to suitably position the height of the container 405, a target object or vehicle can be scanned. For example, as shown in FIG. 4K, the container 405 is positioned at a suitable height to scan a passing car 435 and generate a radiographic scan image of the car 435.

Referring now to FIG. 4L, for transport or redeployment at another site the container 405 needs to be stowed or reloaded onto trailer 410. Thus, trailer 410 is driven so that it is positioned beneath container 405 that is deployed at the surveillance site. If necessary, the height of the container 405 is adjusted by extending the legs 425 vertically so that trailer 410 can be driven unhindered below the container 405. To enable safe positioning of the trailer 410 beneath the container 405 and to avoid bumping of the transportation vehicle into the container, while reverse driving to position the trailer 410 below the container 405, a plurality of safeguards are provided such as a) having a reversing camera on the transportation vehicle, b) having a metal "buffer" behind the driver's cab so that the driver knows when he is in position, and c) having a position sensor on the container 405 (on the wall of the container 405 that faces the reversing transportation vehicle) which actuates when the transportation vehicle is approximately close to correct positioning for reloading the container 405 onto trailer 410.

Once the trailer 410 is positioned below the container 405, the legs 425 are vertically refracted, as shown in FIG. 4M, thereby lowering the container 405 gradually onto the trailer 410. FIG. 4N shows the container 405 in a stowed position on trailer 410. Once on trailer 410, the legs 425 are fully retracted vertically; thereafter, legs 425 are fully retracted horizontally to lie within the vertical recesses 420.

In accordance with an aspect of the present invention, a moving target (such as a vehicle) can also be scanned while the container is in stowed position on the stationery trailer. FIG. 4O shows the container 405 stowed on the stationery trailer 410 while a truck 445 passes by. The passing truck 445 is scanned to produce a radiographic image thereof. In one embodiment, the height of the container 405 when in stowed position on the trailer 410 corresponds to height 306 of FIG. 3.

Figure 5A:
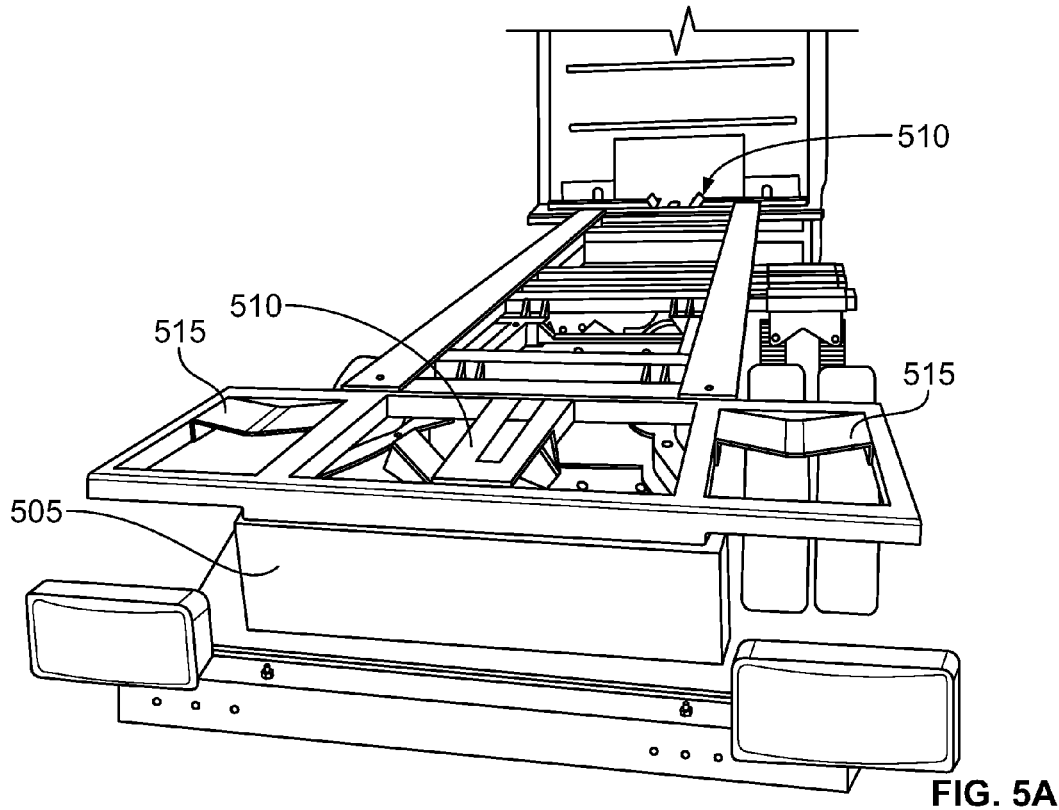
FIG. 5A illustrates a trailer chassis equipped to safely stow the container, in accordance with an embodiment.

The chassis of the trailer is suitably equipped to ensure that the container, encasing the X-ray inspection system, is safely stowed onto the chassis for transportation as well as for scanning targets while stowed on the chassis. In one embodiment, as shown in FIG. 5A, the trailer chassis 505 is equipped with a pair of container mounting brackets 510 located at the front and rear of the chassis 505, as well as four 'V' shaped container locating plates 515, one located at each corner of the chassis 505. As shown in FIG. 5B, the four locating plates 515 and corresponding rollers 520 (at the base of the container 525) ensure that the container 525 aligns with the front and rear mounting brackets 510 when being lowered onto the chassis 505. In one embodiment, after the container 525 has been lowered onto the chassis 505, the four legs 530 move inboard to the stowed position and are held in place by an angled plate 535 located on each of the four leg assemblies 530. The angled plate 535 on the inboard end of each leg 530, locates into a cradle on each side of the mounting bracket 510, securing the container 525 in the stowed position on the chassis 505.

FIG. 6 is a schematic representation of a radiation source and detector assembly 600 known in the art that may be used in the inspection system of the present specification. In one embodiment, the assembly 600 comprises an X-ray source, in the form of a rotating disc X-ray source 602. An object to be scanned is shown in the form of a truck or lorry 604. In one embodiment, a detector 606 is arranged on the same side of the truck or lorry as the source. The source is arranged to irradiate a single region of the object at any one time (i.e. in any one irradiation event or burst). The source produces a tightly collimated pencil beam 608 which irradiates a point on the object 604. Radiation 610 is scattered in all directions and is detected at the detector 606. The detector 606 measures the amount of radiation per irradiation event in order to provide information on the point of the object being irradiated during that event.

In another embodiment, the X-ray source employed in the inspection system of the present specification comprises a multi-element scatter collimator to produce a fan beam of X-rays for irradiating the object being scanned; backscattered X-rays from the object being detected by a segmented detector array located behind the multi-element collimator and comprising one detector element corresponding to each collimator element. Such an X-ray source is described in U.S. patent application Ser. No. 13/368,202, assigned to the Applicant of the present specification, and herein incorporated by reference in its entirety.

In yet another embodiment of the present specification, an X-ray backscatter source detector assembly is combined with a high intensity linear accelerator based transmission imaging source detector assembly, in order to spatially correlate surface X-ray backscatter imaging with bulk object transmission imaging as a further investigation in detection of illicit materials and objects in cargo items.

Figure 7A:
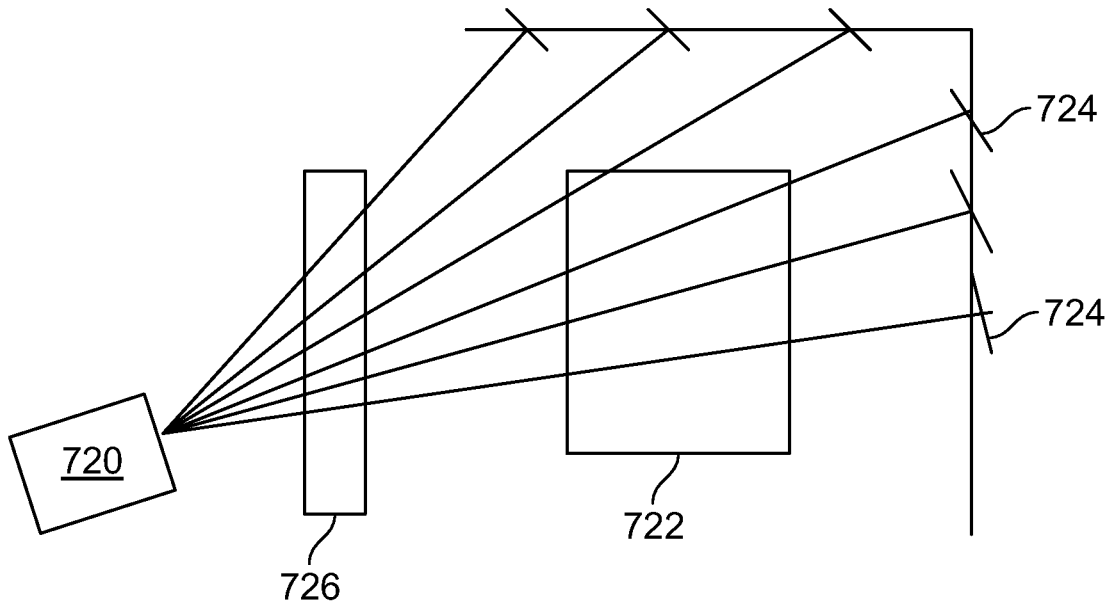
FIG. 7A illustrates a source/detector assembly, in accordance with an embodiment of the present specification.

FIG. 7A illustrates a source detector assembly, in accordance with an embodiment of the present specification. Here, an X-ray linear accelerator (linac) 720 is used to fire a collimated fan-beam of high energy (at least 900 keV) radiation through an object 722 under inspection and towards a set of X-ray detectors 724 which can be used to form a high resolution transmission X-ray imaging of the item under inspection. The X-ray linear accelerator beam is pulsed, so that as the object under inspection moves through the beam, the set of one-dimensional projections can be acquired and subsequently stacked together to form a two-dimensional image. In this embodiment, an X-ray backscatter detector 726 is placed close to the edge of the inspection region on the same side as the X-ray linear accelerator 720 but offset to one side of the X-ray beam so that it does not attenuate the transmission X-ray beam itself In accordance with an alternate embodiment, the source 720 is a low energy X-ray tube source with energies in the range of 60 keV to 450 keV.

As mentioned above, it should be noted herein that the radiation source can be, in alternate embodiments, one or a combination of Gamma-ray, microwave, optical, radio frequency, millimeter wave, terahertz, infra-red and ultrasound radiations in addition to high and low energy X-ray.

Figure 7B:
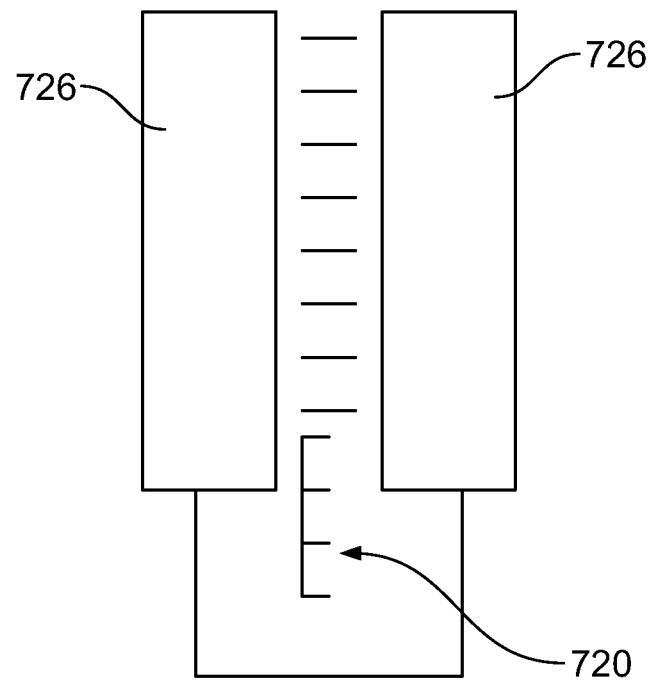
FIG. 7B illustrates a source/detector assembly, in accordance with another embodiment of the present specification.

FIG. 7B illustrates a source detector assembly, in accordance with another embodiment of the present specification. It is advantageous to use two backscatter imaging detectors 726, one on either side of the primary beam. In some embodiments the backscatter detectors may be arranged differently. In some embodiments there may be only one backscatter detector. In other embodiments there may be more than two such detectors. X-ray inspection systems employing such a backscatter source detector assembly are described in U.S. patent application Ser. No. 12/993,831, assigned to the Applicant of the present specification, and herein incorporated by reference in its entirety.

In another embodiment, the present specification provides a multi-view source/detector assembly comprising four discrete backscatter source detector assemblies that re-use the pencil beam from one backscatter system to illuminate large area detectors from a second backscatter system so that simultaneous multi-sided backscatter and transmission imaging using the same set of four X-ray beams can be achieved.

Figure 8:
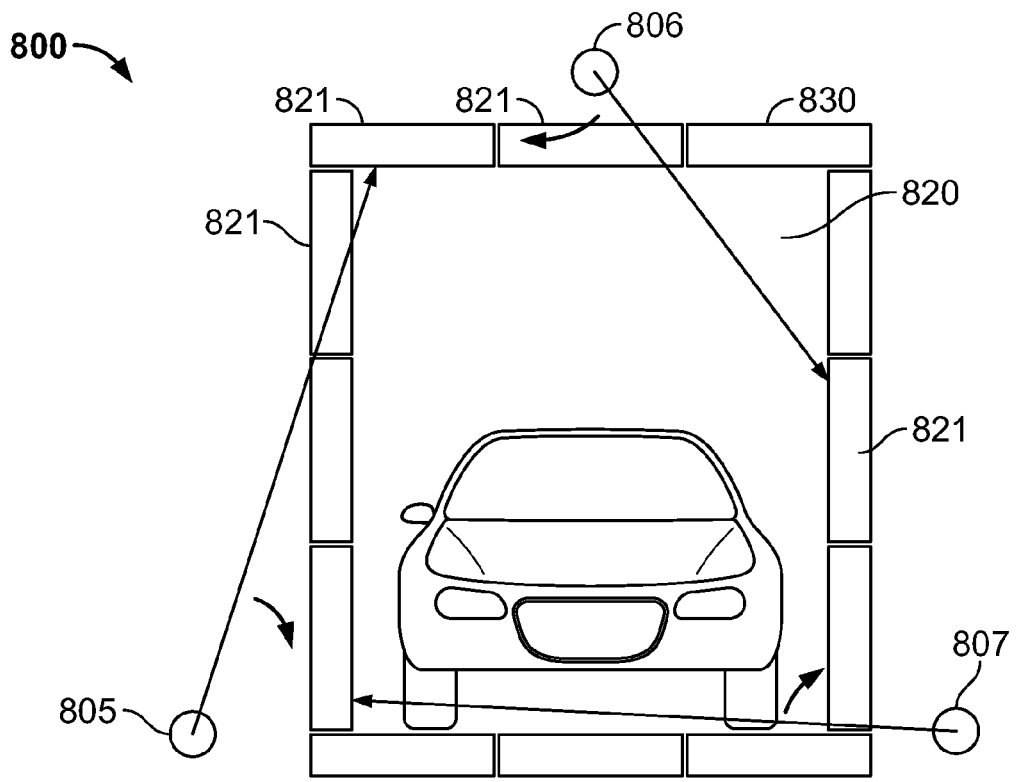
FIG. 8 is a multi-view X-ray source detector assembly employed in the X-ray inspection system, in accordance with an embodiment of the present specification.

FIG. 8 is a multi-view X-ray source detector assembly employed in the X-ray inspection system, in accordance with an embodiment of the present specification. In one embodiment, system 800 has a three-view configuration enabled by three simultaneously active rotating X-ray beams 805, 806 and 807 with plurality of detectors placed correspondingly, in one embodiment, in transmission configuration to form a scanning tunnel 820. System 800 provides a high degree of inspection capability, in accordance with an object of the present specification, while at the same time achieving this at substantially low X-ray dose since the volume of space irradiated at any moment in time is low compared to conventional prior art line scan systems that typically have large numbers of pixelated X-ray detectors and fan-beam X-ray irradiation. As shown in FIG. 8, there is almost no cross-talk between the three X-ray views which are collected simultaneously.

Figure 9A:
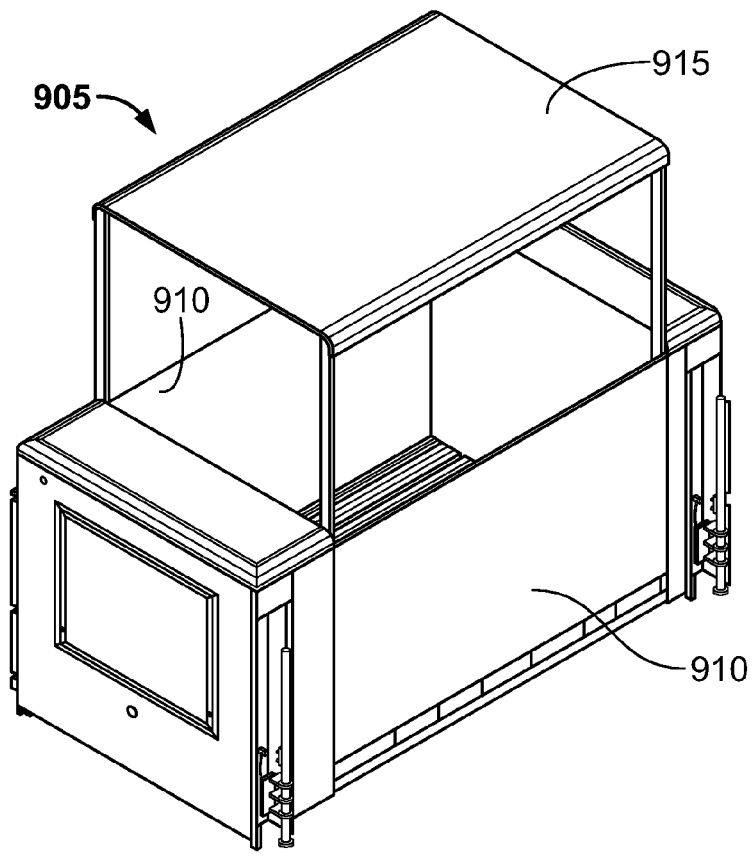
FIG. 9A illustrates an embodiment of a container with extended roof.
Figure 9B:
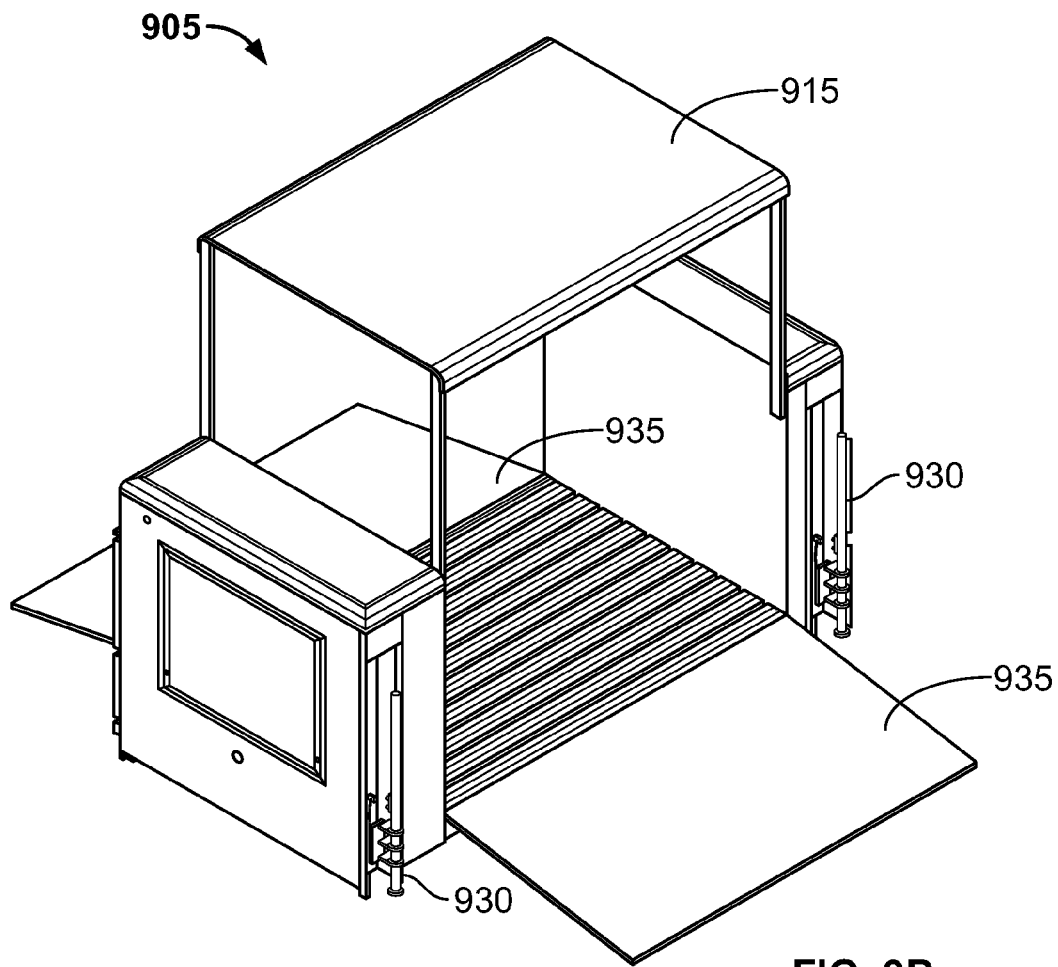
FIG. 9B illustrates the container with folded down side walls and extended roof to form a drive-through portal.

To enable multi-view scanning, in another embodiment, the radiation inspection system of the present invention is operable in drive-through portal format. FIGS. 9A and 9B illustrate an embodiment of a container 905, encasing an inspection system, which has fold-down outer walls 910 and a vertically extendable ceiling 915. As shown in FIG. 9B, once the container 905 is deployed at a surveillance site on four legs 930, ceiling 915 is vertically extended and outer walls 910 (referenced in FIG. 9A) are folded downwards to form a ramp 935 to enable a target vehicle, such as a car, to be driven onto ramp 935 and through the container 905.

Figure 9C:
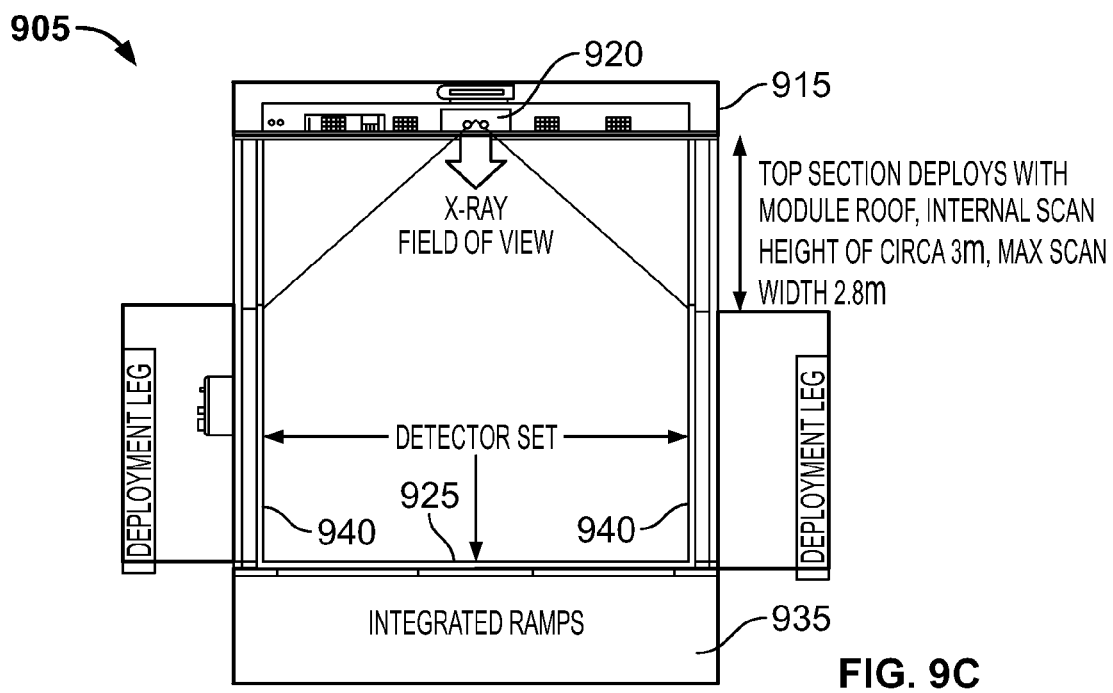
FIG. 9C is a cross-sectional side view of the container with a source/detector assembly, in accordance with an embodiment of the present specification.

FIG. 9C shows a side cross-sectional schematic view of the container 905 formed into a drive-through portal with vertically extended ceiling 915 and folded down walls forming the ramp 935. In one embodiment, an X-ray source 920 is positioned at the ceiling 915 and a plurality of detectors are provided within the container 905. In one embodiment, three detector arrays are strategically positioned: a first detector on floor or base 925 and a second and third detector array positioned within the two fixed walls 940 of the container 905. In further embodiments, one or more detectors are placed at the ceiling 915, such as one on either side of the source 920 to enable the generation of both backscatter and transmission scan images of a target vehicle passing through the container 905. In still further embodiments, additional radiation sources are placed at side walls 940 to enable the multi-view inspection system 800 of FIG. 8.

According to an aspect of the present specification, there is almost no limit to the number of views which may be collected simultaneously in the system 800 with each detector segment 821 being irradiated by no more than one primary X-ray beam at any one time. In one embodiment, the detector configuration 830, shown in FIG. 8, comprises 12 detector segments 821 each of, say, 1m length to form an inspection tunnel of 3 m (Width)×3 m (Height). In one embodiment, the detector configuration 830 is capable of supporting six independent X-ray views to allow transition of the sweeping X-ray views between adjacent detectors. An alternate embodiment comprising 0.5 m long detector segments 821 is capable of supporting up to 12 independent X-ray image views.

Persons of ordinary skill in the art should appreciate that in system 800 of the present specification, volume of detector material is independent of the number of views to be collected and the density of readout electronics is quite low compared to conventional prior art pixelated X-ray detector arrays. Additionally, a plurality of X-ray sources can be driven from a suitably rated high voltage generator thereby enabling additional X-ray sources to be added relatively simply/conveniently. These features enable the high density multi-view system 800 of the present specification to be advantageously feasible in security screening context. Such a multi-view X-ray inspection system has been described in U.S. patent application Ser. No. 13/756,211, assigned to the Applicant of the present invention and herein incorporated by reference in its entirety.

As would be apparent to persons of skill in the art, a plurality of types of X-ray source detector assemblies may be employed in the portable x-ray inspection system of the present specification, such as, but not limited to the exemplary source detector assemblies described above.

Hence, the portable x-ray inspection system of the present specification is a rugged inspection system that may be easily transported from one surveillance site to another without the need for specialized, expensive, transportation vehicles. Further the portable x-ray inspection system is a light weight system which may be encased in a box for transportation and easy deployment at a plurality of surveillance locations.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive.

I claim:

1. An inspection system for screening an object under inspection and configured to be transported on a trailer of a vehicle comprising:
    a container with four walls, four corners, a ceiling and a base that defines an enclosed volume, wherein in a stowed position said container rests on the trailer portion of the vehicle and wherein the trailer portion comprises a bracket;
    at least one radiation source positioned within said enclosed volume, wherein emissions from said radiation source define a field of view;
    at least one detector array positioned within said enclosed volume or physically attached to said container;
    a piston positioned in each of said four corners, wherein each piston is positioned to move horizontally from a first retracted state to an extended state;
    four legs, each of said four legs attached to said piston in each of the four corners, wherein each of said four legs is adapted to be horizontally extendable outwards from each of said four corners and retractable into each of said four corners based upon a horizontal movement of the attached piston, wherein each of said four legs is vertically extendable to at least one height position from ground level; and
    a controller configured to determine said at least one height position using a plurality of data, wherein said plurality of data includes a desired field of view, and to cause each of said four legs to vertically extend to said at least one height position, and wherein at least one the four legs comprises a plate configured to connect to said bracket, thereby securing the container to the trailer.

2. The inspection system of claim 1 wherein said plurality of data further includes at least one of dimensions of the objects under inspection, desired inspection area, detector array configuration, X ray source type, X-ray source configuration, constraining structures, and a presence of people.

3. The inspection system of claim 1, wherein said container further comprises vertical recesses at each of four corners to accommodate each of said piston and leg.

4. The inspection system of claim 3, wherein, in a stowed position, each of said piston and leg rests within said vertical recesses, thereby lying at least partially embedded with respect to the vertical walls of said container.

5. The inspection system of claim 1, wherein in a deployed position, each leg is in contact with the ground and the container is not resting on a trailer portion of a transportation vehicle.

6. The inspection system of claim 1, wherein said at least one source and said at least one detector array are configured to generate scan information from an object under inspection.

7. The inspection system of claim 1, wherein once deployed, each leg is telescopically retracted such that said container is in contact with the ground, and two of said four walls are folded down.

8. The inspection system of claim 1 wherein said ceiling is adapted to be vertically extended upwards to form a drive through portal at said surveillance site.

9. The inspection system of claim 1, wherein said at least one source and said at least one detector array are configured to generate multi-view scan images of an object under inspection.

10. A method of deploying an inspection system comprising: a container with four walls, a ceiling and a base that defines an enclosed volume, wherein said container is stowed on a trailer portion of a transportation vehicle and said trailer portion comprises at least one bracket; at least one radiation source positioned within said enclosed volume, wherein emissions from said radiation source define a field of view; at least one detector array positioned within said enclosed volume or physically attached to said container; and a plurality of legs attached, via pistons, to said container at each of four corners of said container, wherein at least one of said plurality of legs comprises a member that is attached to said bracket, thereby securing the container to said trailer portion, the method comprising:
    using at least one of said pistons, extending at least one of said plurality of legs horizontally outwards from said four corners of said container;
    using a controller, determine a height position for said plurality of legs using a plurality of data, wherein said plurality of data includes a desired field of view;
    based on said determination, extending each of said plurality of legs vertically downwards so that each of said plurality of legs achieves said height position and is in contact with the ground at a surveillance site;
    continuing to extend each of said plurality of legs vertically downwards to enable said container to be lifted off from the trailer portion and be supported fully on said plurality of legs at said surveillance site; and,
    driving said trailer portion away from said surveillance site.

11. The method of claim 10 wherein the height position of said plurality of legs is adjusted to accommodate a plurality of scanning heights.

12. The method of claim 11, wherein said plurality of data further includes at least one of dimensions of the objects under inspection, desired inspection area, detector array configuration, desired field of view, X-ray source type, X-ray source configuration, constraining structures and the presence of people.

13. The method of claim 10 wherein said plurality of legs are adapted to be fully retracted such that said container is positioned at ground level, and wherein two of said four walls of said container are folded down and said ceiling is vertically extended upwards to form a drive through portal at said surveillance site.

* * * * *